(12) United States Patent
Gjertsen et al.

(10) Patent No.: US 12,329,949 B2
(45) Date of Patent: Jun. 17, 2025

(54) CARTRIDGE DEVICES FOR ADMINISTRATION OF A MEDICAMENT

(71) Applicant: ZETEO Biomedical, LLC, Austin, TX (US)

(72) Inventors: Jeffrey Gjertsen, Cedar Park, TX (US); Timothy Sullivan, Austin, TX (US)

(73) Assignee: Zeteo BioMedical, LLC, Austin, TX (US)

( * ) Notice: Subject to any disclaimer, the term of this patent is extended or adjusted under 35 U.S.C. 154(b) by 1056 days.

(21) Appl. No.: 17/327,683

(22) Filed: May 22, 2021

(65) Prior Publication Data

US 2021/0361879 A1    Nov. 25, 2021

Related U.S. Application Data

(60) Provisional application No. 63/029,612, filed on May 25, 2020.

(51) Int. Cl.
| | |
|---|---|
| *A61M 5/315* | (2006.01) |
| *A61M 5/19* | (2006.01) |
| *A61M 5/24* | (2006.01) |

(52) U.S. Cl.
CPC .......... *A61M 5/31585* (2013.01); *A61M 5/19* (2013.01); *A61M 5/24* (2013.01); *A61M 5/31505* (2013.01); *A61M 5/31526* (2013.01)

(58) Field of Classification Search
CPC ...... A61M 5/31585; A61M 5/19; A61M 5/24; A61M 5/31505; A61M 5/31526; A61D 1/02; A61D 7/00
See application file for complete search history.

(56) References Cited

U.S. PATENT DOCUMENTS

| | | | |
|---|---|---|---|
| 4,447,223 A * | 5/1984 | Kaye | A61M 37/0069 604/61 |
| 6,708,846 B1 | 3/2004 | Fuchs et al. | |
| 8,377,009 B2 | 2/2013 | Sullivan et al. | |
| 2002/0007149 A1* | 1/2002 | Nelson | A61M 5/30 977/956 |
| 2002/0032409 A1* | 3/2002 | Ritsche | A61M 15/0081 604/153 |
| 2006/0243275 A1 | 11/2006 | Ruckdeschel | |
| 2008/0210228 A1 | 9/2008 | Corbacho | |
| 2014/0148755 A1* | 5/2014 | Fontana | A61D 1/025 604/62 |
| 2017/0000594 A1* | 1/2017 | Buckley | A61D 1/02 |
| 2019/0358010 A1* | 11/2019 | Holmes | A61M 31/00 |

OTHER PUBLICATIONS

International Search Report and Written Opinion issued in relation to International Application No. PCT/2020/025076.

* cited by examiner

*Primary Examiner* — Dung T Ulsh

(57) ABSTRACT

A handheld assembly for dispensing a medicament to a subject is provided. The assembly includes a unit dose cartridge device, a shell, a plunger, a dispense button, a drive member and an escapement that is movable and capable of cycling the dispense assembly thru multiple states of a dispense cycle.

20 Claims, 21 Drawing Sheets

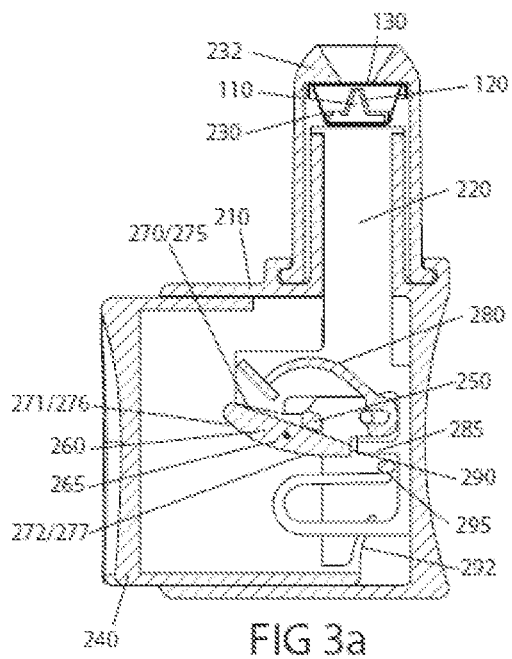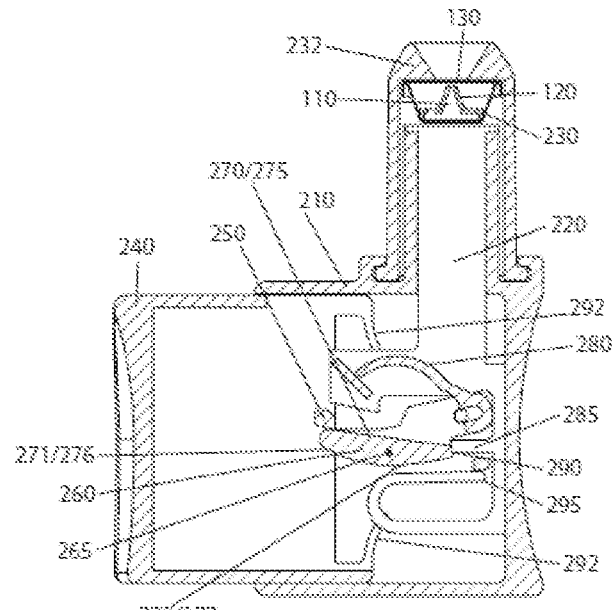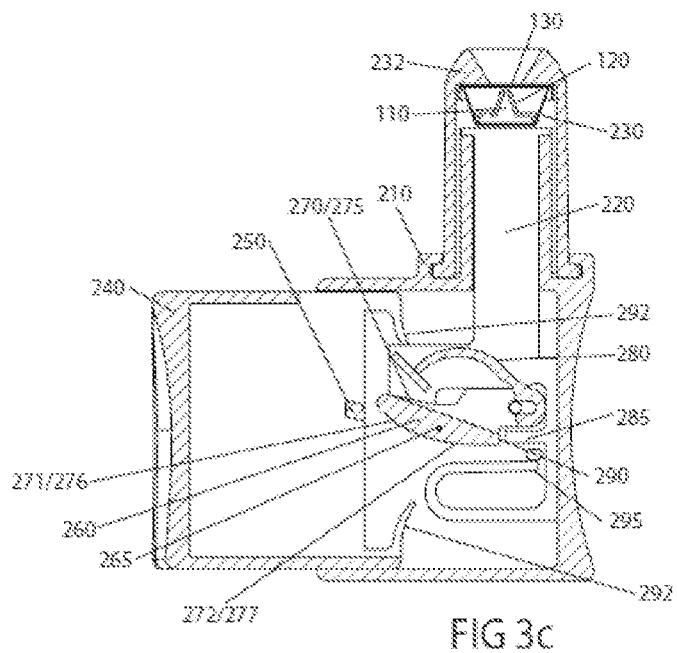

CARTRIDGE DEVICES FOR ADMINISTRATION OF A MEDICAMENT

CROSS REFERENCE TO RELATED APPLICATIONS

This application claims priority and benefit from U.S. Provisional Patent Application Ser. No. 63/029,612 filed on Mar. 25, 2020, for "Cycling Plunger Device and Method for Administration of a Medicament," the content of which is incorporated in its entirety herein by reference.

BACKGROUND OF THE INVENTION

Technical Field

Embodiments of the subject matter disclosed herein generally relate to medical devices and systems for administering medicaments to a human or animal subject; more particularly, hand operated devices and systems for dispensing a unit dose form containing a medicament to a subject.

Discussion of the Background

Certain diseases and medical conditions that are systemic, neurological or local are treatable via the administration of drugs and therapeutic agents taken topically or systemically through the eye, ear, mouth, nose, lungs or dermal skin layer. A number of pharmaceutical or biologic agents are deliverable as liquids, suspensions, emulsions, powders or particles orally to the lungs, sublingual, buccal or intra-nasally (including nose to brain), and may be administered for topical, systemic or intracranial deposition, including but not limited to antibiotics, antipyretics, anti-inflammatories, beta-blockers, biologics, biosimilars, cannabinoids, vitamins, botanicals, co-factors, enzymes, inhibitors, activators, nutrients, vaccines including DNA based killed or live virus or microorganisms, nucleic acids, proteins, peptides, antibodies, peptide mimetics, prophylactic or therapeutic immune-modulators, anti-viral and anti-bacterial compounds, biologics, diagnostic agents and other agents, pharmaceutical compositions, botanicals or medicaments.

Hand operated devices (either as single use or multi-use devices) have been developed to deliver dose quantities where each expression by hand of the device delivers an individual dose. For example, Fuchs et al. U.S. Pat. No. 6,708,846 teaches a reusable dispenser unit and a media container for a medicament for intranasal administration. The device has a release button and a compressed spring that pushes against a rod and discharges the drug. Ritsche et al. U.S. Pat. No. 6,725,857 claims a multi-dose strip of blisters sequentially expressed by a device with a spring-loaded firing button attached to a pretensioned storage element that rotates a conveying drum. Sullivan et al. U.S. Pat. No. 8,377,009 discloses handheld devices with a sliding mechanism and an angled cam attached to a firing button which activates a plunger for discharging a crushable unit dose ampule or blister.

However, available devices suffer from several pitfalls including overly complex mechanisms prone to jamming and/or inconsistent dose delivery. Thus, there is a need for improved devices that are user friendly and reliable.

SUMMARY OF EXAMPLE EMBODIMENTS

According to an embodiment, there is a handheld assembly for dispensing a medicament to a subject, the assembly includes a shell housing at least partially a dispense button, a drive member in communication with the dispense button, a plunger, and an escapement member having at least one ramp surface. The assembly also includes a unit dose cartridge comprising more than one cylindrical blister chambers each configured to house a unit dose form containing a medicament. The shell further comprises a cartridge alignment channel open on opposite ends and configured to slidably accept the unit dose cartridge. Depressing the dispense button causes the drive member to translate along a ramp of the plunger escapement member extending the plunger to express the unit dose form.

According to another embodiment, there is a handheld assembly for dispensing a medicament to a subject, the assembly includes a shell configured for housing components of the handheld assembly; a unit dose cartridge comprising more than one cylindrical blister chambers configured to each house a unit dose form containing a medicament; a plunger at least partially enclosed within the shell and extending from the shell and configured to express a unit dose form; a dispense button at least partially enclosed within the shell and extending from the shell and in slidable communication with the shell; a drive member located within the shell and in communication with the dispense button; and a plunger escapement member movable about an axis within the shell and having more than one ramp wherein each ramp has a predetermined profile. A first motion of the dispense button causes the drive member to translate along a first ramp of the plunger escapement member readying the assembly for dispense, and a second motion of the dispense button causes the drive member to translate along a second ramp of the plunger escapement member extending the plunger to express the unit dose form.

According to yet another embodiment, there is a handheld assembly for dispensing a medicament to a subject, the assembly includes a shell configured for housing components of the handheld assembly; a clip receivable within the shell, the clip comprising a housing containing more than one stackable unit dose cartridge wherein each cartridge is comprised of more than one cylindrical blister chambers configured to each house a unit dose form containing a medicament; a plunger at least partially enclosed within the shell and extending from the shell and configured to express a unit dose form within the cartridge; a dispense button at least partially enclosed within the shell and extending from the shell and in slidable communication with the shell; a drive member located within the shell and in communication with the dispense button; a plunger escapement member (260) movable about an axis (265) within the shell and having a plurality of ramp surfaces (270).

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 3A thru 3C show an exemplary handheld assembly during the make ready stage.

DETAILED DESCRIPTION OF EXAMPLES OF THE INVENTION

Figure 1A:
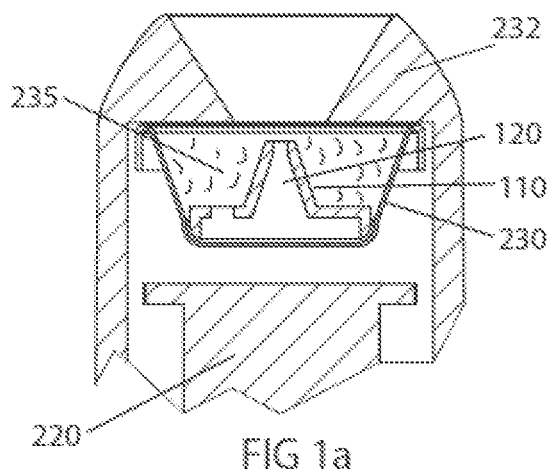
FIG. 1A thru 1E illustrate an exemplary set of stages of dispense.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to devices and systems for precisely controlled dose delivery of a medicament to a subject. However, the embodiments discussed herein are not limited to such elements.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the described features, structures or characteristics may be combined in any suitable manner in one or more embodiments.

The following is a limited list of examples of general classes of medicaments administered through the nasal or oral cavity or topically to the eye, ear or skin as liquids, solutions, suspensions, emulsions, powders or reconstituted powders for a host of indications which can include but not limited to anemia, asthma, bronchitis, rhinitis, flu, coronavirus, cancer, cystic fibrosis, diabetes, inflammation, osteoporosis, hepatitis, arthritis, chronic or acute pain, immunodeficiency disorders, multiple sclerosis, endocrinological disorders, neurodegenerative disorders, ocular disorders, metabolic disorders, man-made or naturally occurring bioterror threats, dermal disorders and wounds, etc. Drug compounds for treating those indications include various adjuvants, calcitonin, erythropoietin, heparin, inhibitors, insulin, interferons, interleukins, hormones, neurotropic agents, growth factors, stimulating factors, vasodilators and constrictors, antibiotics, antipyretics, anti-inflammatories, biologics, probiotics, vitamins, co-factors, enzymes, inhibitors, activators, nutrients, aptamers, thioaptamers, anti-virals, immuno-modulators, diagnostic agents, vaccines including killed or live virus or microorganisms, nucleic acids, synthetic messenger RNA (s-mRNA), proteins, peptides, antibodies, peptide mimetics, micro or nanoparticles. This list is not intended to be exhaustive and in no way is inclusive of all possible conditions and diseases, drugs and compounds, or routes or targets of administration, but rather is to illustrate the breadth of medicaments and other agents and indications employable in the present invention and contemplated by the present disclosure. For simplicity, the various agents dispensable by devices and system of the present disclosure will herein be referred to as medicaments which is intended to encompass pharmaceutical and non-pharmaceutical agents.

Blister-based unit dose forms provide a safe, convenient, sterile, easily stored and transported, and controlled dose platform to deliver those medicaments to a subject via a target route of administration. The devices and assemblies that express the unit dose forms can provide for simplified self-administration by a user or may be administered by a medical professional to a subject. A subject may be a human or non-human animal.

However, as explained in detail below, the unit dose forms require a simple but precise device in order to provide an accurate, full, efficient (low waste), and repeatably consistent dose to a subject. Thus, it is desirable that the dispensing device perform precisely through each stage of the dose dispense sequence. Moreover, the device should preferably be operable by hand, include single as well as reusable embodiments and thus be capable of delivering sequential precise doses to a subject.

The unit dose forms and cartridges containing said unit dose forms of the present disclosure, in preferred embodiments, are comprised of crushable blisters. Note herein that said dosage forms are commonly referred to in the art using alternative terms, such as forms, units, unit dose or unit dosage forms, blisters, blister packs, blister wells, wells, chambered wells, ampoules, primary containers, or similar terminology. The dosage forms described herein generally as "unit dose", "unit dose forms", "wells", "blisters" or "chambered wells", etc. are used interchangeably and are intended to encompass the full scope of known formed receptacles commonly in use for medicament substance storage and delivery.

The manufacturing processes for forming unit dose forms in a continuous web can include a step of drawing a metal, polymer, or laminated metal-polymer foil or other suitable sheet of material with the appropriate mechanical characteristics to allow hot, warm or cold forming and drawing are known in the art and contemplated herein. In certain embodiments, one or more forming pins can be used to form a primary contour, the contour having a depth of at least 100% and up to 150% of the depth of the final formed recess or well. A second stage involves shaping the primary contour with one or more of the same or additional forming pin(s) to the desired formed recess depth and shape, with a depth that is less than the depth of the primary contour, while substantially maintaining the surface area of the primary contour formed in the first stage. The contour or shape of the blister well can be formed to contain certain shape features, indentations, or be imparted with texture by the forming pins to provide for a means of securing the internal piercing device within the blister well or recess.

The formed well or recess is then typically loaded aseptically with the predetermined quantity of medicament or other material for administration to a subject and in certain preferred embodiments disclosed herein, an internal piercing device is placed into the formed well. A lidding material (or "lidstock") of the same or similar laminated material as the blister well or other sheeting material is then rolled atop the well and bonded to the well sheeting with adhesives, or by pressure, thermal, ultrasonic or other welding means.

In certain embodiments, the individual dose forms that can be formed in sheets which are in later manufacturing steps, singulated into individual doses for use in single-use, disposable, non-reloadable devices, or for use in devices which are reloadable with additional unit doses for subsequent dosing of the same or different subject(s). Alternatively, and depending upon the application and indication, the sheets may be formed and cut into rows, arrays, grids or other configurations of blisters suitable for use in multi-dose devices or cartridges to be used in such devices. Numerous commercially available laminated structures can be manufactured using known materials and methods which facilitate the production of variable strength of seal between opposing faces, are known in the art and are readily contemplated by the present disclosure.

Regardless of the shape, size, or geometric configuration of the unit dose form; in certain preferred embodiments each unit dose contains an internal piercing device member. The internal piercing member can be manufactured by techniques known by those skilled in the art, for example injection molding or machining. The piercing member can be constructed of any material with suitable chemical compatibility and mechanical properties to impart the design strength characteristics examples include ceramic, glass, metal, composites, polymeric plastics etc. In preferred embodiments the internal piercing member may be constructed from polymeric materials to include but not limited to polyethylene (PET), polypropylene, polyetherimide (PEI), polysulfone (PSU), polyaryletherketone (PAEK), polystyrene, or poly ether ether ketone (PEEK), self-reinforced polyphenylene (SRP) or other pharmaceutical or medical grade material or materials.

In preferred embodiments, the internal piercing members are typically injection molded as single piece components, however in certain other embodiments where particular structural features (to be described in greater detail below) are less amenable to one-piece molding; the piercing members can be assembled from multiple machined, printed and/or molded parts. For example, certain embodiments may entail attaching by press fit, friction fit, snap fit, or threading a machined metal or separately molded elongated tip to a plastic base part. Other combinations of parts, manufacturing methods, materials, and assembly methods are known in art and fully contemplated herein. In preferred embodiments, the elongated tip of the piercing member may contain at least one internal channel which provides a high velocity liquid stream and serves as a nozzle for dispensing a medicament as a liquid spray or dispersed powder. According to other embodiments, the elongated tip may be solid (i.e. no internal channel), but the surface may include striations, ribs, spirals or the like to aid in dispersion of a powder once the elongated tip pierces the lidstock.

Figure 1B:
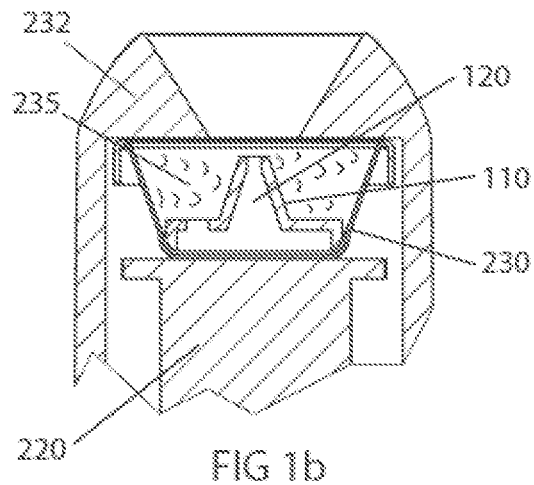

An overview of a set of stages for the dispensation of a medicament utilizing a handheld assembly with a plunger and other components acting upon a unit dose form are shown in FIGS. 1A-E. The initial stage as shown in FIG. 1A is typically characterized as the "ready to load" stage, whereby a plunger 220 is first positioned to accept a dispense tip 232 preloaded with a unit dose form 230 containing a medicament 235, The unit dose forms as shown contain an internal piercing member 110 which in preferred embodiments itself includes an internal channel 120 for passage of the medicament 235. Once the unit dose is loaded and the plunger 220 is in contact with the unit dose 230 as shown in FIG. 1B; the device is prepared for activation, which may be referred to as "ready to dispense", or "make ready" stage or state.

Figure 1C:
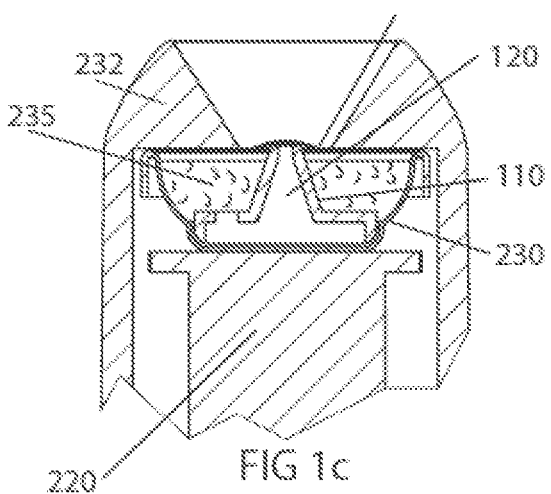
Figure 1D:
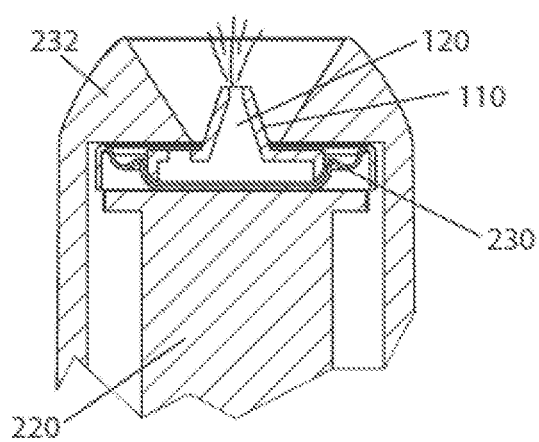

In the "activation" or "dispense" stage, the plunger is acted upon by other device components, the sequence of which will be described in detail below. Plunger 220 further extends and begins to pressurize the unit dose form 230 as shown in FIG. 1C. In this next stage, as the unit dose form 230 begins to breach the unit dose form's lidding material 130 until it punctures and the internal channel 120 of the internal piercing member 110 is now in communication with the exterior. Once punctured, the pressurized medicament 235 within the unit dose enters the internal piercing member 110 internal channel 120. The stage shown in FIG. 1D is where the unit dose form 230 is crushed and medicament 235 exits the unit dose and is dispensed to a subject via the desired route of administration.

Figure 1E:
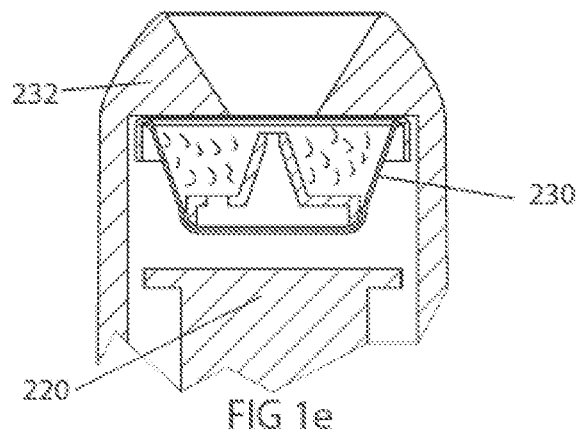

Finally, once the medicament is dispensed to a subject, the assembly in certain embodiments may be undergo one or more steps in order to be returned to its original state ready for another dispense. This stage will be referred to as the "return" stage and is shown in FIG. 1E.

There are several key dispense characteristics impacted by the design of the device components, particularly the plunger action which generates the internal pressurization and expression of the contents out of the unit dose form, Those performance characteristics include, for example, the dispense efficiency, defined as the fraction of the dose actually dispensed; the characteristics of the dispense spray (droplet size, droplet distribution, spray pattern, plume geometry etc.); the degree of cross contamination between unit dose forms occurring as a result of holdover medicament remaining within or upon the unit dose form following dispense; as well as the convenience and ease of a users experience with the device, among other aspects.

Figure 2:
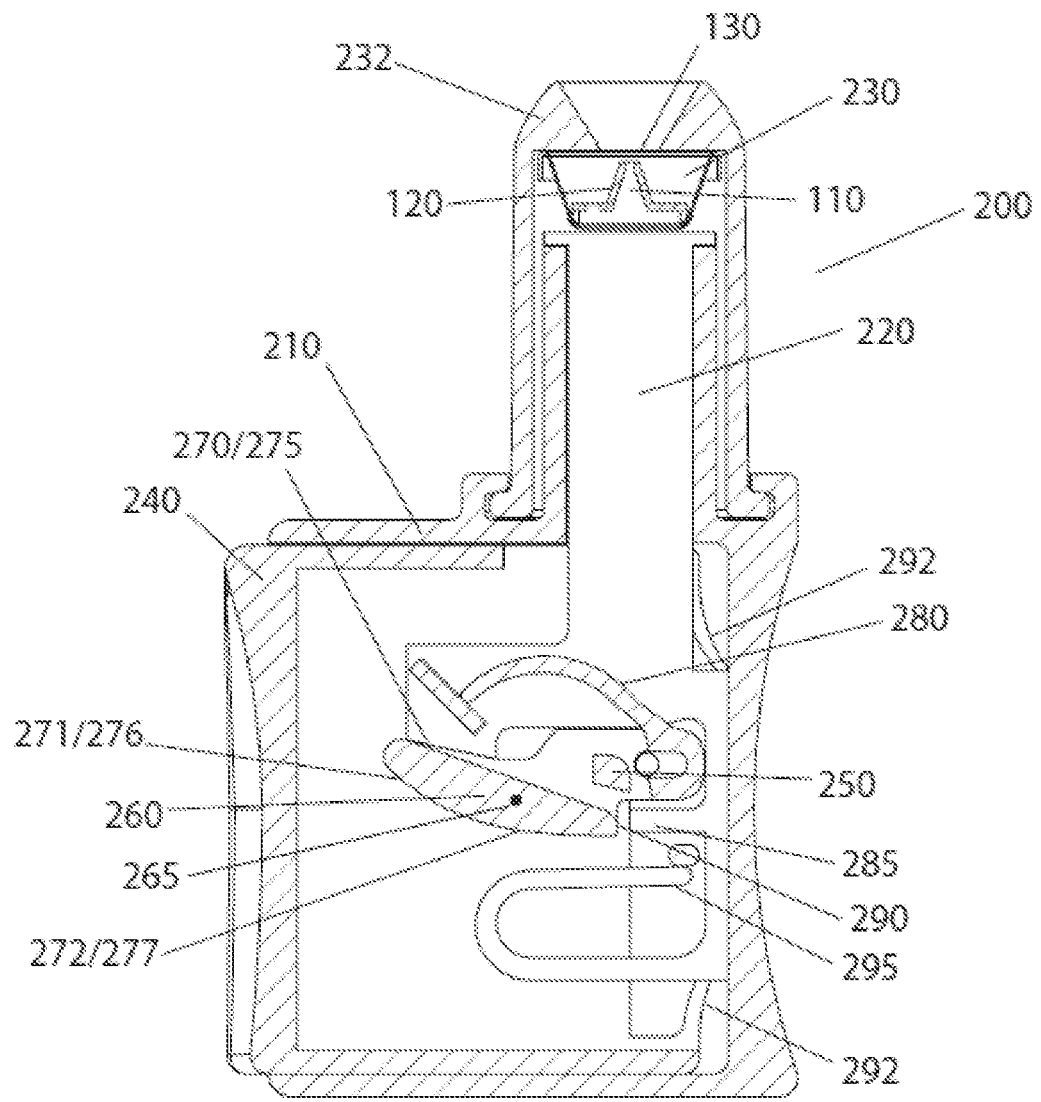
FIG. 2 shows an exemplary handheld assembly in its initial stage.

An exemplary handheld assembly for administering a medicament to a subject is shown in FIG. 2. The assembly 200 comprises a shell 210 for housing components of the handheld assembly. Shell 210 may be comprised of two halves (one half is shown) which are injected molded and snap fitted together, for example. A plunger 220 is at least partially enclosed within shell 210 and extends from the shell and configured to express the unit dose form 230 containing a medicament 235. In preferred embodiments, unit dose form 230 is contained within a dispense tip 232 that is configured to attach to the shell 210. Also, in preferred embodiments, unit dose form 230 also contains an internal piercing member 110 which itself includes an internal channel 120.

A dispense button 240 is at least partially enclosed within shell 210 and extends from the shell and is slidable between the shell halves when acted upon by a users hand. A drive member 250 is located within shell 210 and is in communication with dispense button 240 and in preferred embodiments drive member 250 is comprised of a post or other protrusion attached to or molded as part of dispense button 240.

A plunger escapement member 260 (hereinafter "escapement") is also contained within shell 210 and is movable (rotatable and/or translatable) about an axis 265 within shell 210, Escapement 260 may be a polygonal body having multiple sides which comprise at least one ramp 270 upon its surface (four ramps 270, 271, 272 and 290 are shown in this example). The escapement 260 may be a solid or hollow molded or machined body. In the context of the present disclosure, an escapement shall refer to device or body that provides mechanical linkage between at least one source body to at least one other receiver body. Such devices are used to provide a step wise mechanical action when acted upon by an energy source. Each ramp 270 upon its surface has a predetermined profile 275 comprised of a radius of curvature, a linear slope or combination of the two in one or more sections upon the surface. Each ramp 270 is configured to provide a defined action when drive member 250 translates along its surface, to be described below in greater detail.

Assembly 200 may also include a plunger escapement member return spring 280; a plunger hold surface 285; a reset ramp surface 290; a dispense button return spring 292 at the base dispense button 240, and a plunger return spring 295 all of which are to be described in detail below.

The assembly as shown in FIG. 2 is in its initial stage characterized as "ready to load" meaning plunger 220 is in a retracted and able to accept dispense tip 232 with unit dose 230. Dispense button 240 is also in a retracted state meaning it is substantially withdrawn within shell 210. Escapement 260 is in its initial static position as well.

In the "make ready" stage as shown in FIGS. 3A-C, dispense button 240 is extended, i.e., withdrawn from shell 210 which causes drive member 250 to make contact with (FIG. 3A) and then translate along a first ramp 270 on the upper surface of escapement 260. In an exemplary embodiment, first ramp's 270 predetermined profile 275 is a single section with a constant slope, though other profiles may be contemplated. For example, as shown in the figures, second ramp 271, though comprising a single side or face of escapement 260, has two ramp sections (271 and 272) of varying profile (276 and 277, respectively) whereby a first section 271 has an initial curvature or radius, followed by a second section 272 of a substantially flat or linear slope.

As escapement 260 is acted upon by translating drive member 250, it (escapement 260) rotates around an axis 265 (not shown behind escapement body), moving it out of the way of the drive member 250. FIG. 3B shows dispense button 240 extended and drive member 250 at left edge of escapement 260. Once dispense button 240 is fully extended and drive member 250 is clear of escapement 260, as shown in FIG. 3C, escapement spring 295 will move the escapement 260 back to its position, thus placing the assembly in a make ready state.

Figure 4A:
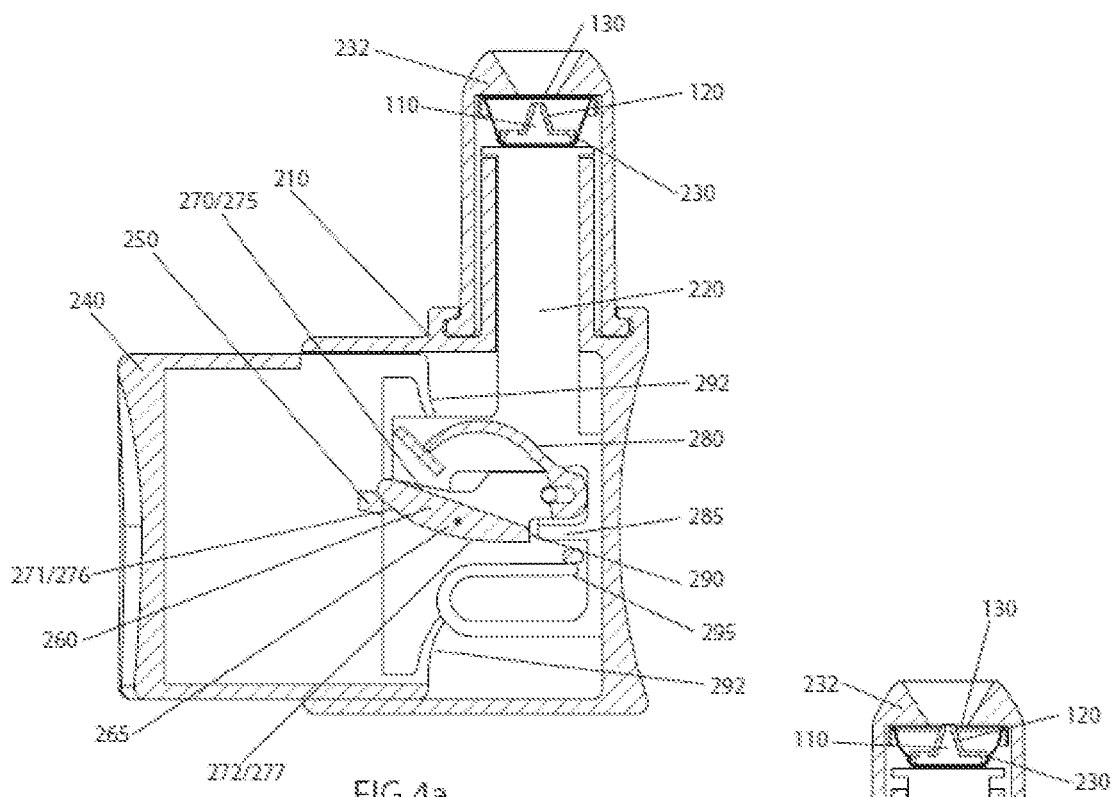
FIGS. 4A and B show an exemplary handheld assembly during early dispense stage.
Figure 4B:
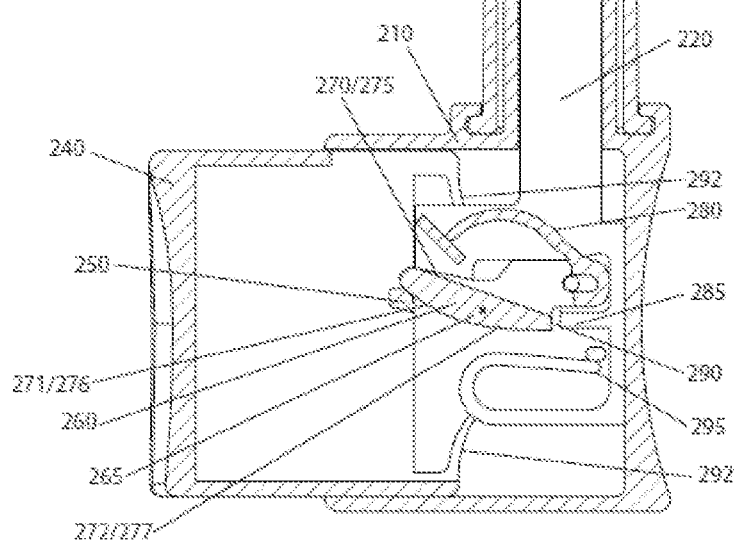

At the beginning of the dispense activation stage, as shown in exemplary FIG. 4A, dispense button 240 is depressed into shell 210 which causes drive member 250 to travel back towards escapement 260 until it engages with a second ramp 271 on the escapement's underside (in this embodiment) with a separate predetermined profile 276. As dispense button 240 is continued to be depressed, as shown in FIG. 4B, drive member 250 translates along second ramp 271 which causes escapement 260 to contact and extend plunger 220 thus compressing unit dose 230.

Figure 5:
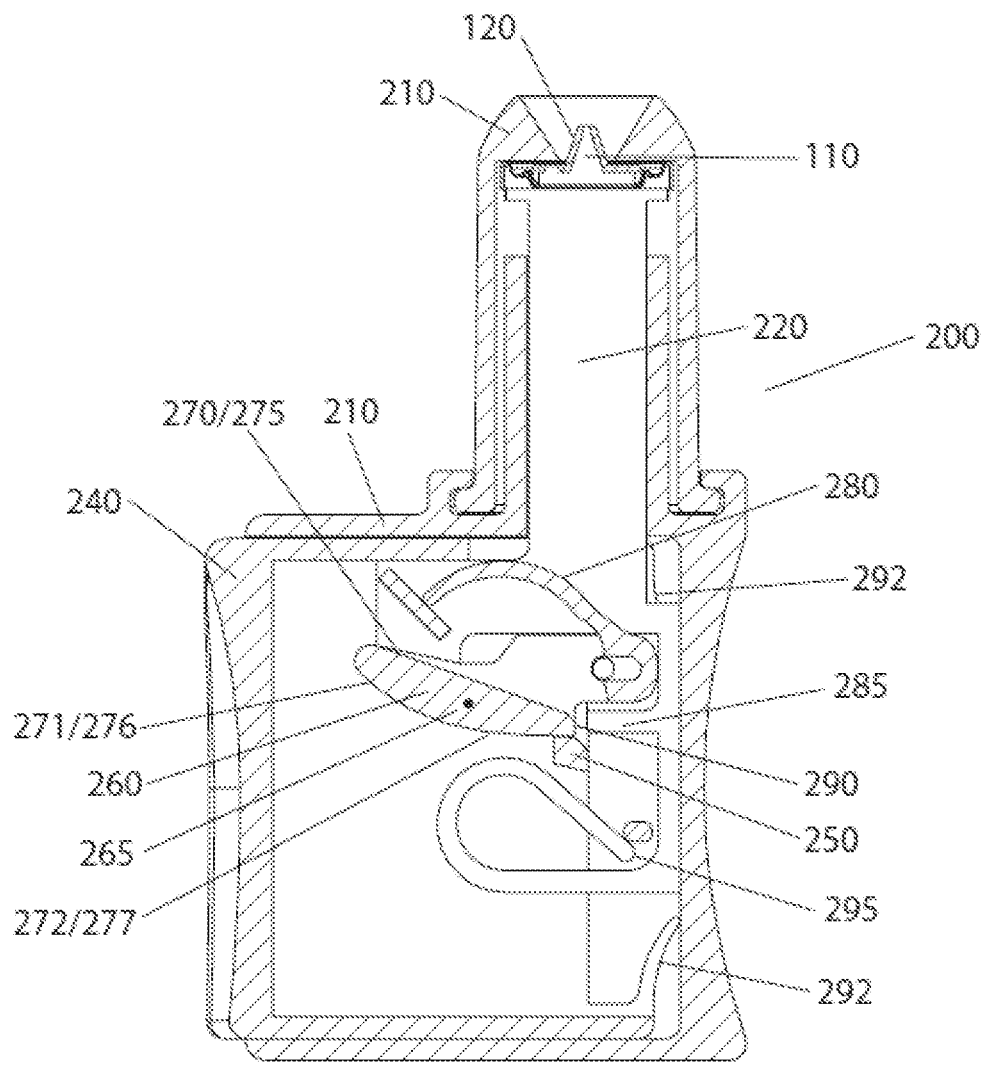
FIG. 5 shows an exemplary handheld assembly drive member translating along a second ramp during dispense.
Figure 6:
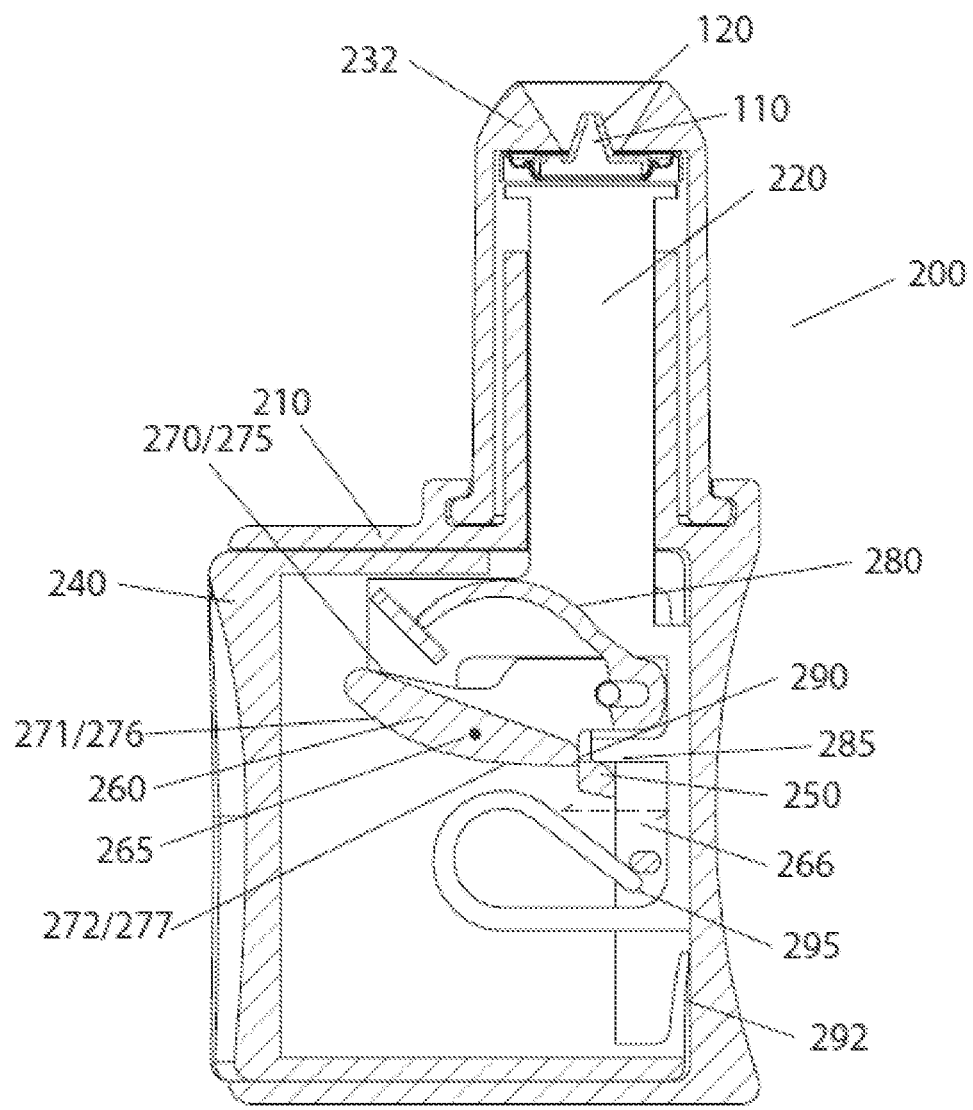
FIG. 6 shows an exemplary handheld assembly drive member engaging a plunger hold surface during dispense.

As shown in FIG. 5, drive member 250 continues to translate along the second ramp 271 during the dispense activation until it reaches the end of the second ramp while plunger 220 continues to compress unit dose 230 and dispensing medicament 235. Prior to drive member 250 reaching the end of second ramp 270, plunger return spring 295 engages with shell 210, Optionally, when drive member 250 reaches the end of second ramp 270, drive member 250 engages with plunger hold surface 285 near the base of plunger 220 as shown in FIG. 6. Plunger hold surface 285 serves as stopping point in the dispense which allows drive member 250 to hold the plunger in an extended position until dispense button 240 is released.

Figure 7:
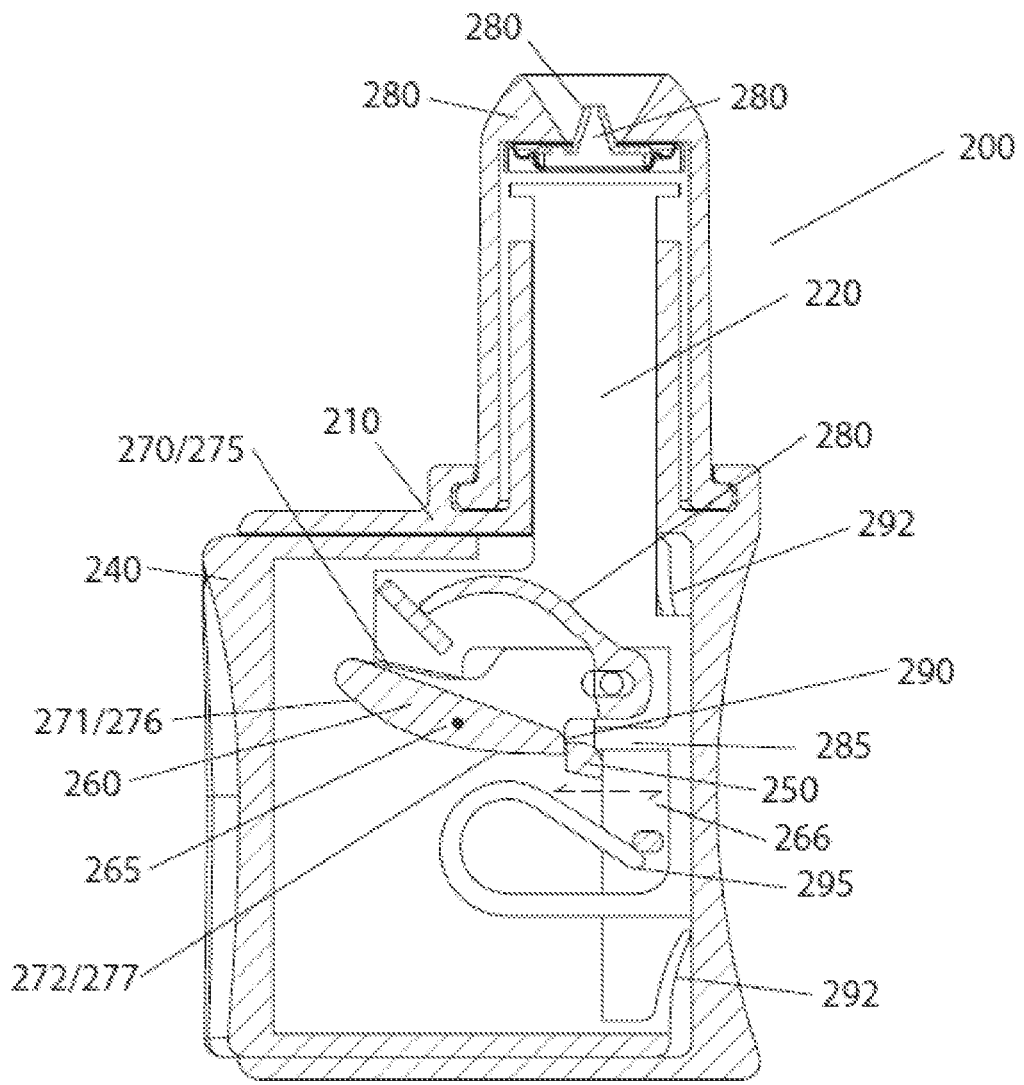
FIG. 7 shows an exemplary handheld assembly drive member engaging a reset surface during dispense.

In certain preferred embodiments, at the end of the dispense stage, dispense button 240 is released by the user, and one or more dispense button return springs 292 will push dispense button 240 outward from shell 210 causing drive member 250 to press out on reset surface 290 located on the end of escapement 260 as shown in FIG. 7. In this embodiment, the reset surface 290 comprises a fourth ramp on escapement 260, which acts as turning point for drive member 250 to reverse direction. In this embodiment, escapement 260 may move in a translational motion along axis 266 (depicted by arrows) in a vertical direction when acted upon by plunger return spring 295.

Figure 8:
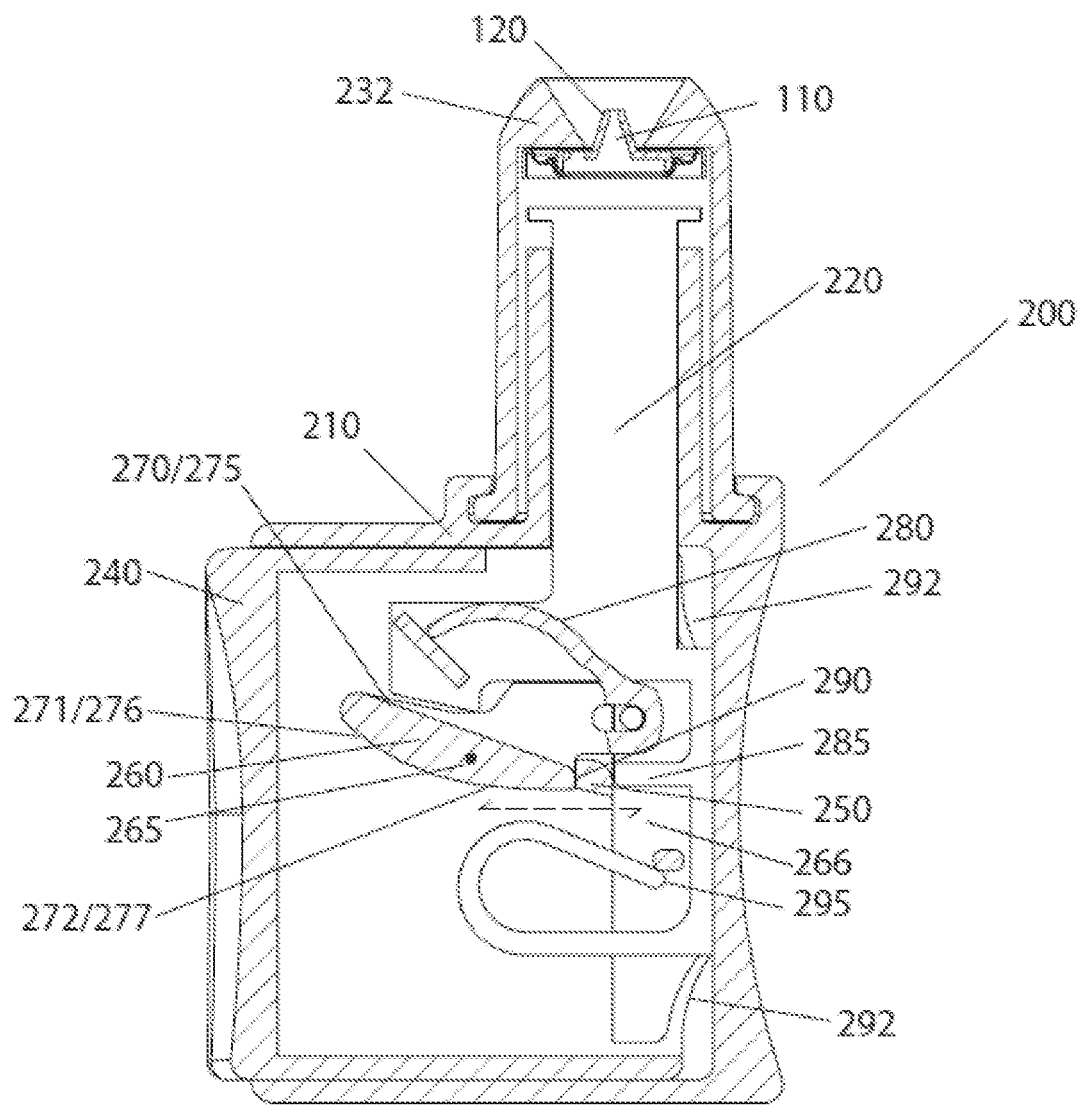
FIG. 8 shows an exemplary handheld assembly drive member passing in between the escapement and plunger hold surface during dispense.
Figure 9:
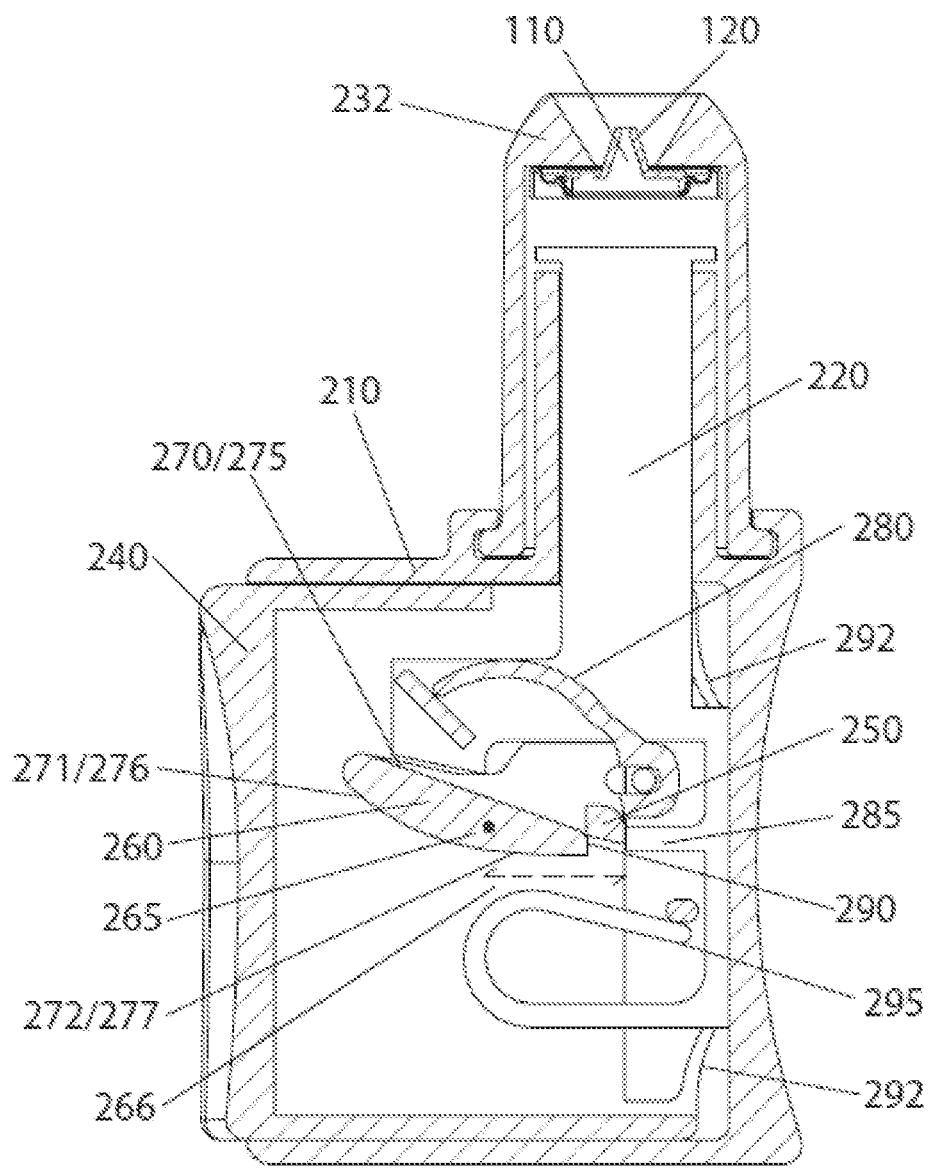
FIG. 9 shows an exemplary handheld assembly with its mechanisms returned to their original state following dispense.

Escapement 260 will move along this second axis 266 until there is enough space between the second ramp 270 on the escapement and the plunger hold surface 285 for drive member 250 to pass between the two bodies as shown in FIG. 8. When this occurs, plunger 220, driven by plunger return spring 295, will retract back to its static position and escapement 260 will return to initial state (i.e, "return" stage) position once reset surface 290 has been cleared. At this point the dispenser assembly 200 has returned with all of the mechanisms in their original state prepared for a subsequent cycle of dispense (FIG. 9).

As shown in the figures, plunger return spring 295 may be comprised of a partial loop attached to a surface within inner shell 210 body, and in other embodiments it may be attached to dispense button 240. It may be molded as a single part or attached or welded as a separate part and may be comprised of the same or different material.

Similarly, as shown for example in FIG. 7, the dispense button return spring 292 may be provided as a feature molded together with the dispense button 240 and typically comprised of a curved surface capable of bending and thus storing energy as a spring.

Also as shown, for example, in FIG. 5, certain embodiments of the assembly may include a plunger escapement return spring 280. At the end of the dispense, once dispense button 240 is released, this spring acts to pull back or reverse plunger 220. This action is beneficial for avoiding or reducing cross contamination among unit dose forms, particularly between those dispensed and those awaiting dispense in a multi-dose embodiment. A dispensed unit dose form has a tendency for surface tension and other charge effects to cause a droplet of the medicament material to remain at the tip; typically partially within and outside the internal channel 120 of the internal piercing member 110 once it has punctured the unit dose 230 lidstock. As discussed earlier, the unit dose form 230 is typically comprised of metal and polymer laminates which while crushable, retain some elasticity under deformation. When spring 280 draws back plunger 220 following dispense, the unit dose form 230 elastically expands, drawing inward the adhering droplet of medicament where it largely remains, dries and is thus unable to transfer to other unit doses or other surfaces of the dispense assembly.

Other embodiments are readily contemplated by the disclosure herein. For example, assembly 200 may be configured for single use whereby escapement 260 is comprised of a single ramp 270 for dispense or include two ramps one for "make ready" (270) and one for dispense (271). In this embodiment, dispense button 240 may originate in extended form and thus already configured ready to dispense, or non-extended and thus for compactness retractable for "make ready" staging prior to dispense. In both these single-use embodiments, the dispense button following dispense may be pressable back into the housing following dispense, again for compactness, without cycling the device components for another dose.

Figure 10A:
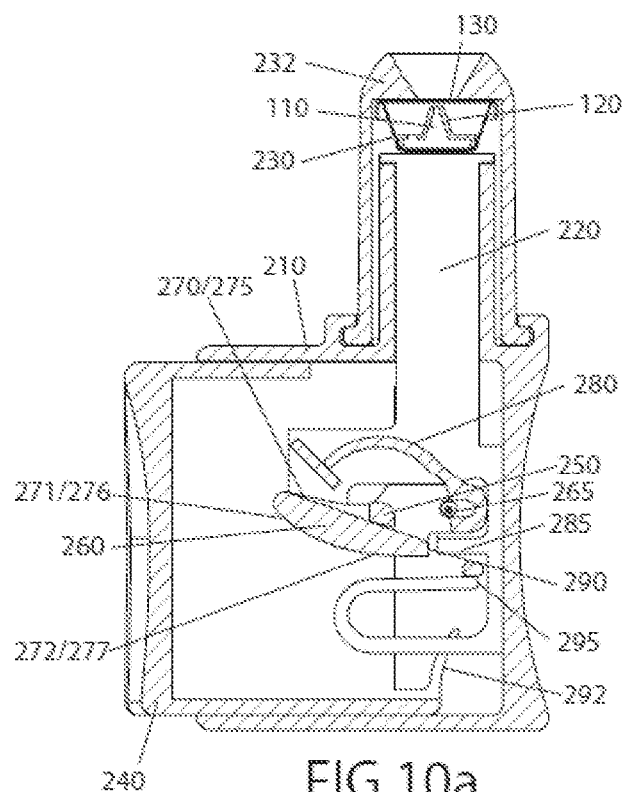
FIGS. 10A and B show an exemplary handheld assembly with an alternative escapement embodiment.
Figure 10B:
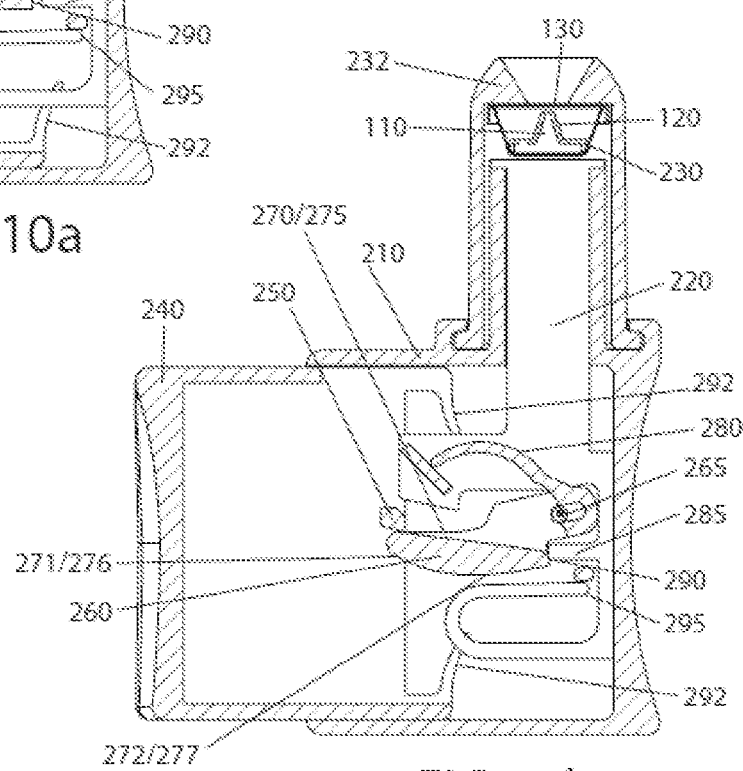

In yet other embodiments, plunger escapement member 260 may pivot at one or more different axes points as shown for example in FIGS. 10A and 10B. Here, axis 265 is located away from the main body of escapement 260 whereby a pin may translate within a slotted portion of the base of plunger escapement return spring 280. As shown in FIG. 10A, as dispense button 240 is withdrawn during the early portion of the make ready stage, drive member 250 moves along ramp surface 270 and escapement 260 pivots downward about axis 265 located to the rear (in the right in the figure) of the escapement. FIG. 10B depicts drive member 250 near the end of ramp 270 with escapement 260 rotated downward, dispense button 240 fully withdrawn and the assembly in a make ready state.

Figure 11:
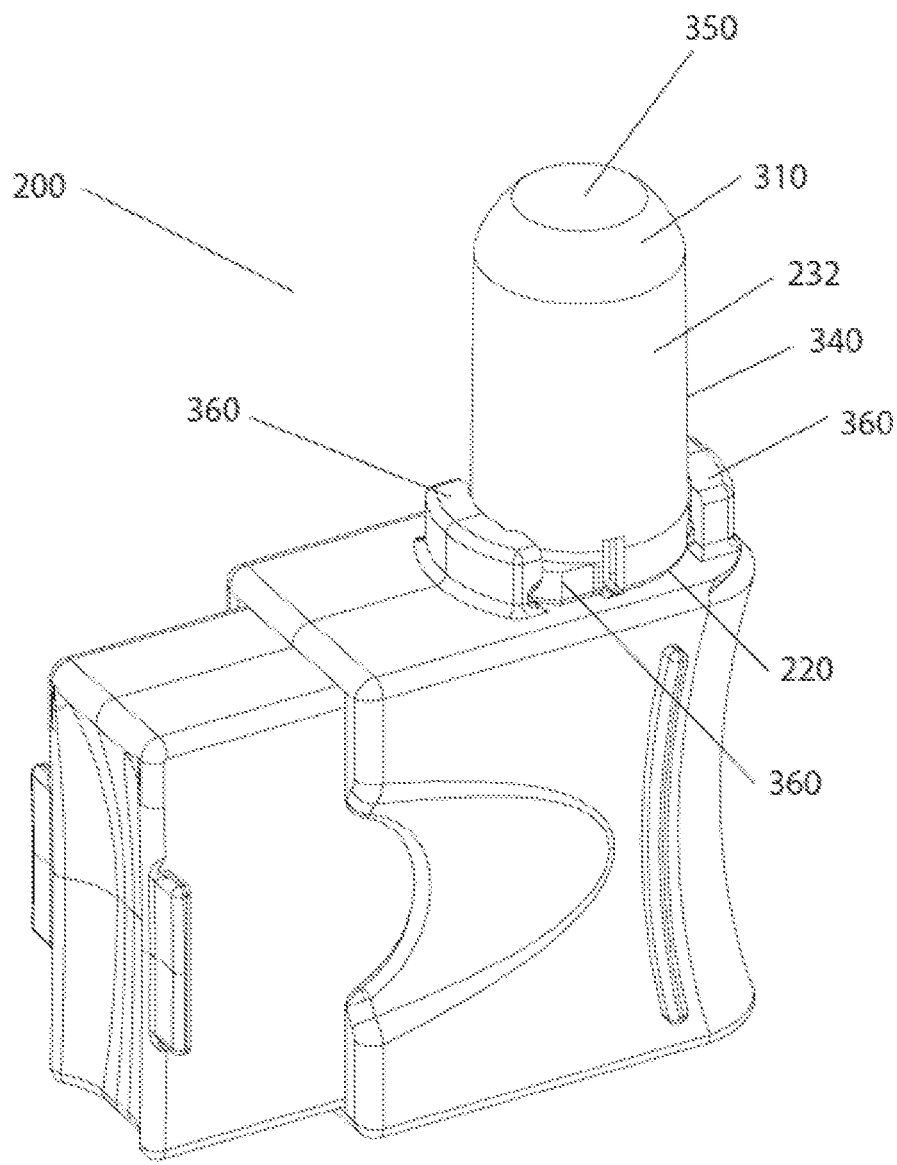
FIG. 11 shows an exemplary handheld assembly with an interlocking dispense tip.

In multi-use, reusable embodiments, assembly 200 may further comprise a removable dispense tip as shown in FIG. 11. Dispense tip 232 includes a unit dose form 230 (not shown) containing a medicament 235 (not shown) as in previous embodiments. In preferred embodiments, unit dose form 230 includes an internal piercing member 110 with an internal channel 120. The unit dose is preloaded in the distal end 310 of a dispense tip 232 which in this embodiment has a cylindrical hollow body 340 along its axis. The distal end 310 may be domed or other shape configured to receive and interact with unit dose 230 and has a thru hole 350 from which the medicament is dispensed to a subject.

One or more splines 360 may be located upon an upper surface of shell 210 and proximate and at least partially circumferential to the opening in shell 210 for plunger 220, Splines 360 may be semi-circular with a radius similar to that as the plunger 220 opening and are configured to rotatably interlock with one or more tabs 370 located at the lower end of body 320 of dispense tip 232. The tabs 370 and splines 360 thus provide for the ability to removably affix the dispense tip to the shell for reloadable operation.

Figure 12:
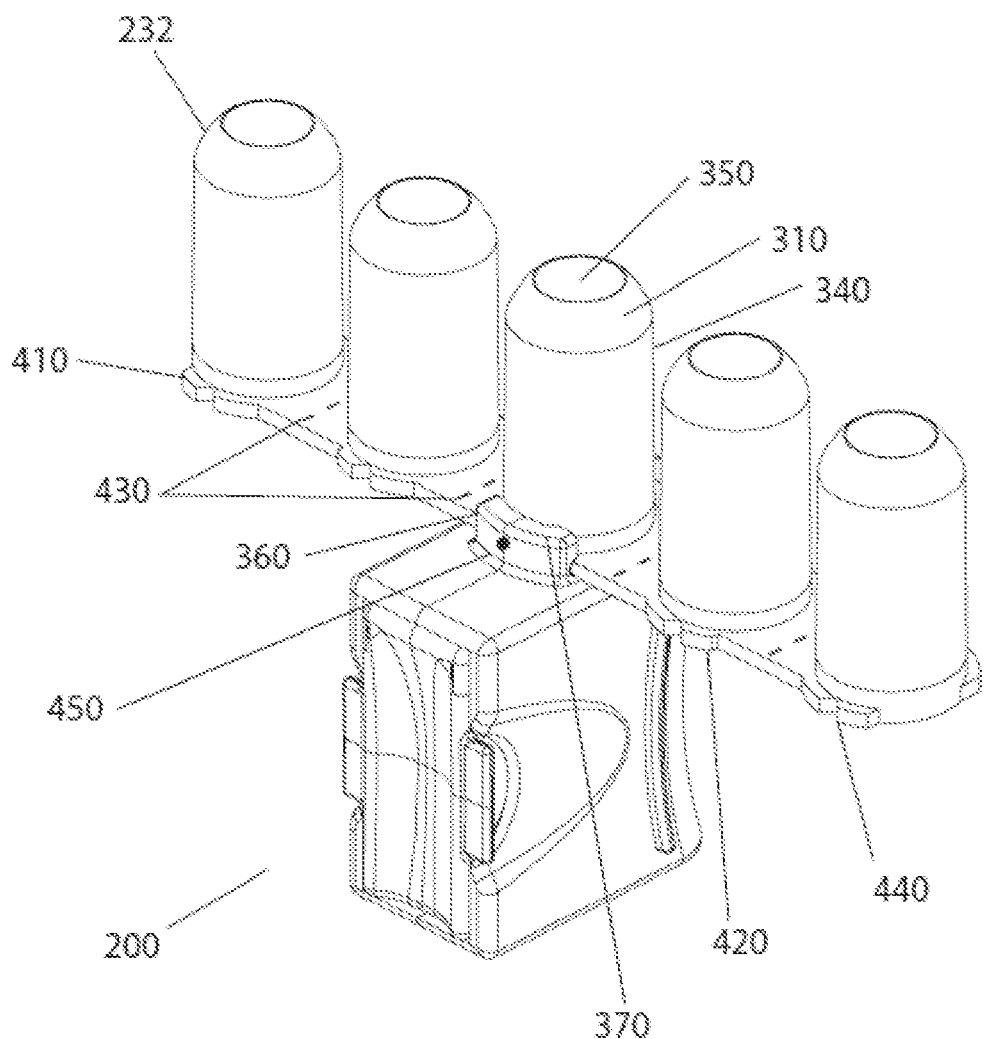
FIG. 12 shows an exemplary handheld assembly with a strip of interlocking dispense tips.

In yet other embodiments, for example as shown in FIG. 12, the dispense tip 232 may be configured in strips 410 comprising a linear array of more than one preloaded dispense tip 232. In this embodiment, dispense tip 232 tabs 370 are replaced by two oppositely located continuous lips 420 configured to slide though splines 360. The strip may be manually loaded and advanced by a user without additional mechanisms for simplicity and cost effectiveness, Lip(s) 420 may also include indentations 440 along their lengths which interact with protrusion points 450 within splines 360 to provide a click sensation as the strip is being advanced to indicate to the user the correct lateral position of next dispense tip.

Thus, in this embodiment with a reusable handheld dispensing assembly with a cycling plunger is provided with a loadable multi-dose array. Further, more than one dispense tip may thus be inexpensively molded together as a single unit and provided in a number to a user according to a particular dosing schedule. The strip 410 may also include separation points 430 in between individual dispense tips to facilitate separation of longer arrays into prescribed numbers, and/or detachment of dispensed doses by a user.

Figure 13:
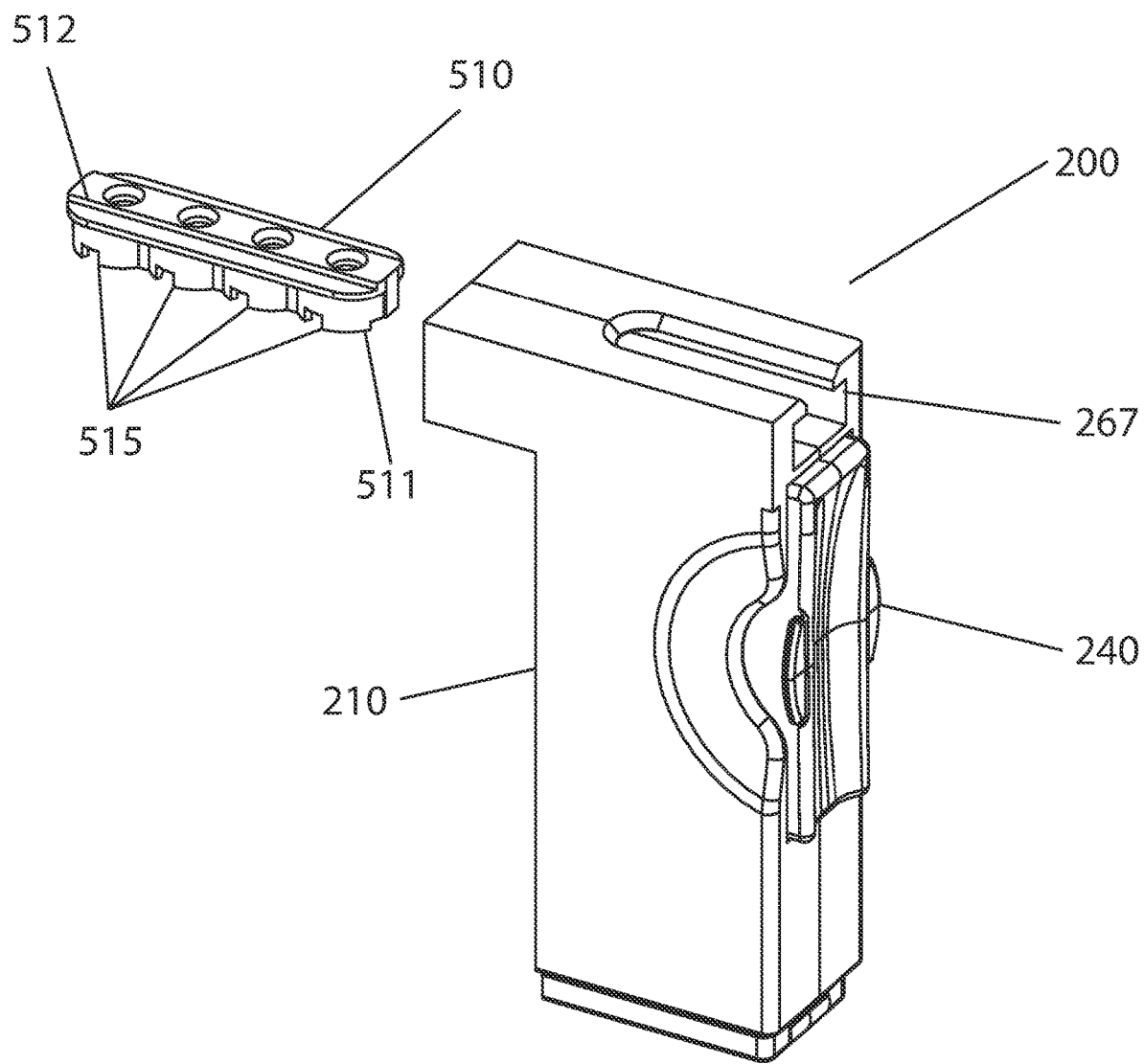
FIG. 13 shows an exemplary handheld assembly with a cartridge of unit doses.

In certain other multi dose reusable embodiments as shown for example in FIG. 13, the unit dose form 230 may be loaded into a cartridge 510 configured to more than one unit dose forms 230 which is then loaded as a unit into the shell 210 of dispenser assembly 200 and sequentially advanced within the shell during the "make ready" step.

As contrasted to earlier described embodiments incorporating individual dispense tips, cartridge 510 comprises a compact housing unit configured to hold a plurality of unit dose forms 230 which may be arrayed in a linear or circular pattern or any other suitable pattern shape, an example of which is shown in FIG. 14. The cartridge 510 in preferred embodiments includes a plurality of cylindrical blister chambers 511 each configured to house and protect an individual unit dose form 230 from damage or inadvertent dispense when cartridge 510 is being handled, stored, and used for dispensing. In preferred embodiments, cartridge 510 with its plurality of blister chambers 511 is molded as a single piece. However, in other embodiments, cartridge 510 may be comprised as a multi-piece construction, for example, as a strip of material configured to accept individual blister chambers by a snap fit or other connection type.

Cartridge 510 may also include a cartridge alignment surface 512 as a raised or elevated section in the form of a longitudinal raised strip that performs as a guide that interfaced with an indented portion of the cartridge alignment channel 267 of the shell 210 (discussed below) thus properly aligning the cartridge 510 inside the shell 210 for dispensing.

Figure 14A:
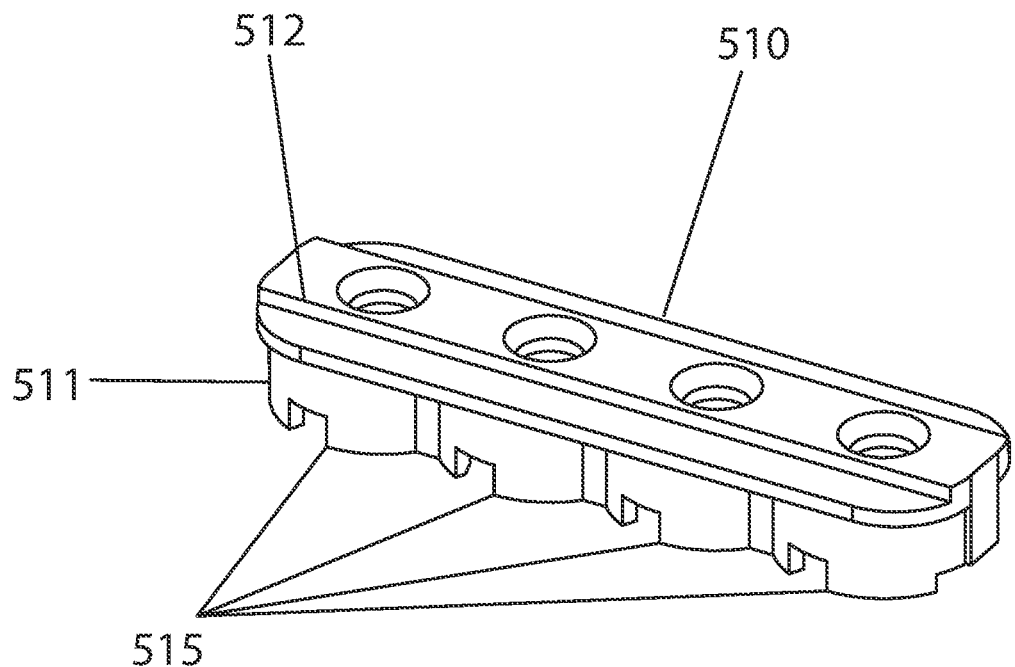
FIGS. 14A and B shows additional views of a cartridge of unit doses.
Figure 14B:
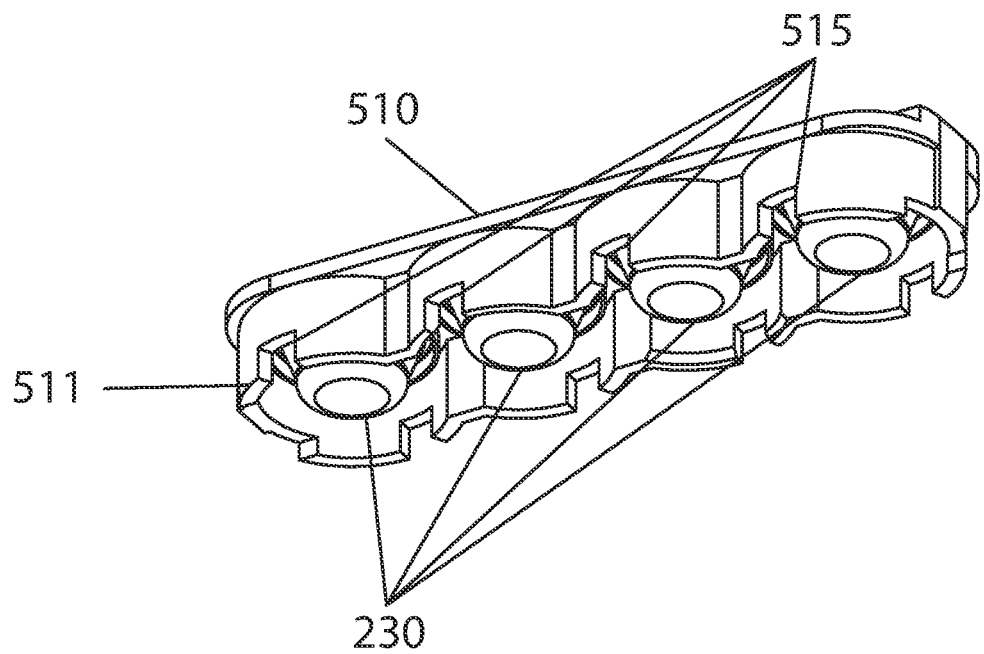

As mentioned, and as also shown in FIGS. 14A and 14B, cartridge 510 typically includes one or more cylindrical blister chambers 511 (four are shown), with each chamber housing a unit does form 230 containing a medicament 235. In preferred embodiments, unit dose form 230 may further include an internal piercing member 110 with an internal channel 120 (not shown but see earlier figures). Further, as described in more detail below, a side wall of a cylindrical blister chamber 511 can be used to advance the cartridge 510 to the next unit dose form 230 for sequential dispensing.

Figure 15:
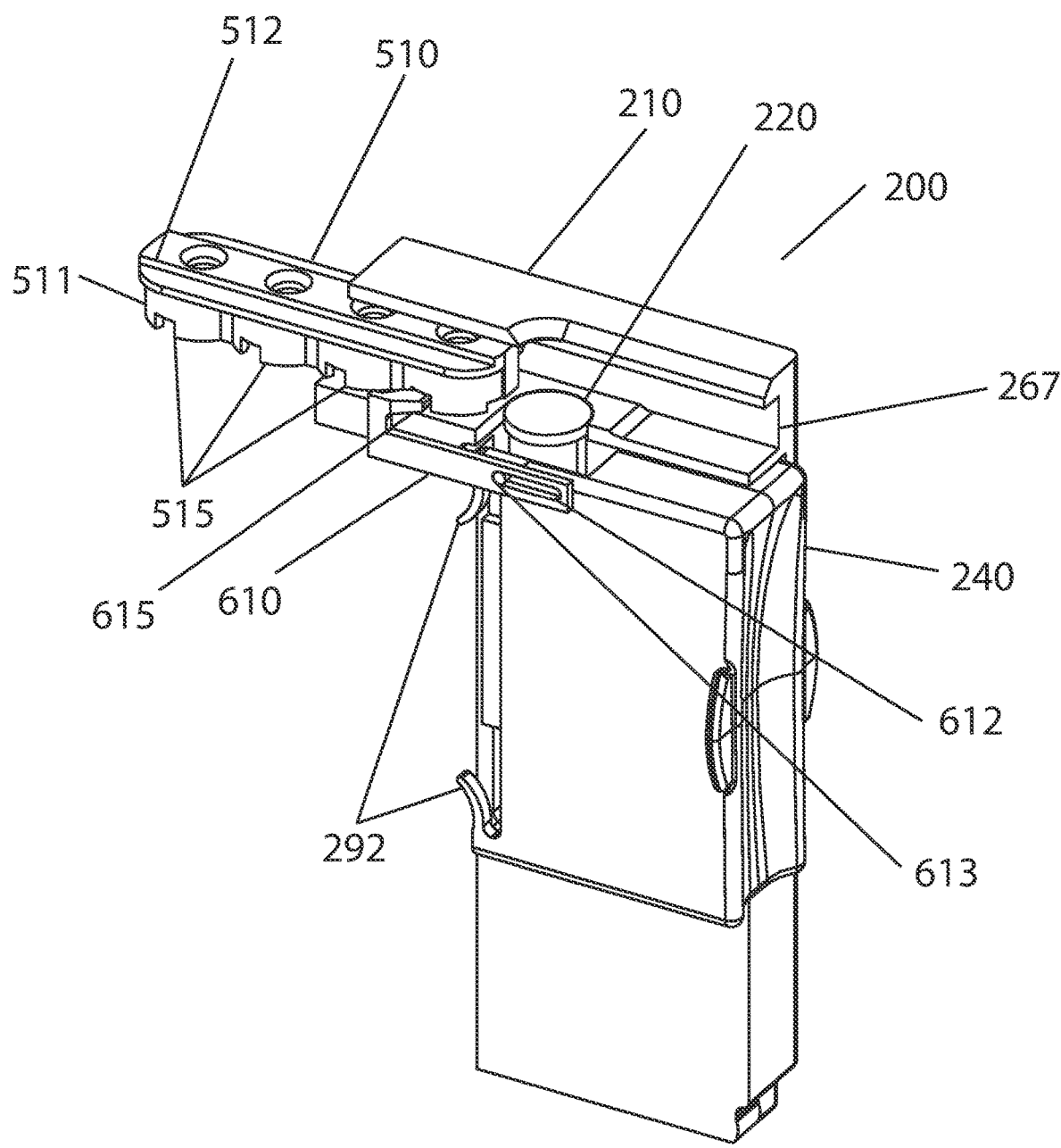
FIG. 15 shows a cutaway view of a cartridge in a handheld device.

In the embodiment depicted in FIG. 15 (with part of shell 210 cutaway for viewing purposes), shell 210 may include a cartridge alignment channel 267 which aligns with the cartridge alignment surface 512 on cartridge 510 to orient the unit dose form 230 correctly relative to plunger 220. The assembly 200 may also include a longitudinal slide arm 610 which is configured to translate cartridge 510 through the cartridge alignment channel 267 of shell 210.

The embodiment of FIG. 15 is shown in the "cartridge loaded" state, with the dispense button 240 retracted into the shell and slide arm finger member 615 interfacing with the notch 515 (discussed below). In preferred embodiments as shown, longitudinal slide arm 610 includes slotted recess 612 on an adjacent end and a slide arm finger member 615 on the distal end, wherein the slotted recess 612 is in communication with the dispense button 240 and the slide arm finger member 615 is configured to slidably advance the unit dose cartridge 510 when the dispense button 240 is withdrawn. Slide arm finger member 615 may be comprised of a tab shaped section protruding or extending at an angle from the distal end of longitudinal slide arm 610. In this embodiment, longitudinal slide arm 610 is illustrated with slotted recess 612 in communication with an engagement pin 613 located on a surface of dispense button 240.

In this manner, slide arm finger member 615 interfaces with a surface of the cartridge, for example in a preferred embodiment, upon successive sidewalls of cylindrical blister chambers 511 to slidably advance the unit dose cartridge 510 within the cartridge alignment channel 267. As shown in FIG. 15, cylindrical blister chambers 511 have a recess or divot in a section of the blister sidewall which acts as a notch 515 for the slide arm finger member 615 to snap into in order to stabilize cartridge 510's position in-between cycles of dose advancement. It also serves as an engagement or lever point for slide arm finger member 615 to pull or advance the cartridge 510.

Longitudinal slide arm 610 is thus in communication with dispense button 240 and is configured to translate the cartridge advancement slide 610 such that a unit dose form 230 within a blister chamber 515 aligns with plunger 220 when the dispense button 240 is withdrawn out of the shell 210. This step is in preparation for expressing a dose as described in detail earlier. Similarly, dispense of a first unit dose 230 by depression of the dispense button 240 causes engagement pin 613 located upon the dispense button 240 to translate within slotted recess 612 of longitudinal slide arm 610 to advance slide arm finger member 615 to a subsequent cylindrical blister chamber notch 515, thus readying the cartridge to pull the next unit dose into alignment with plunger 220.

Figure 16:
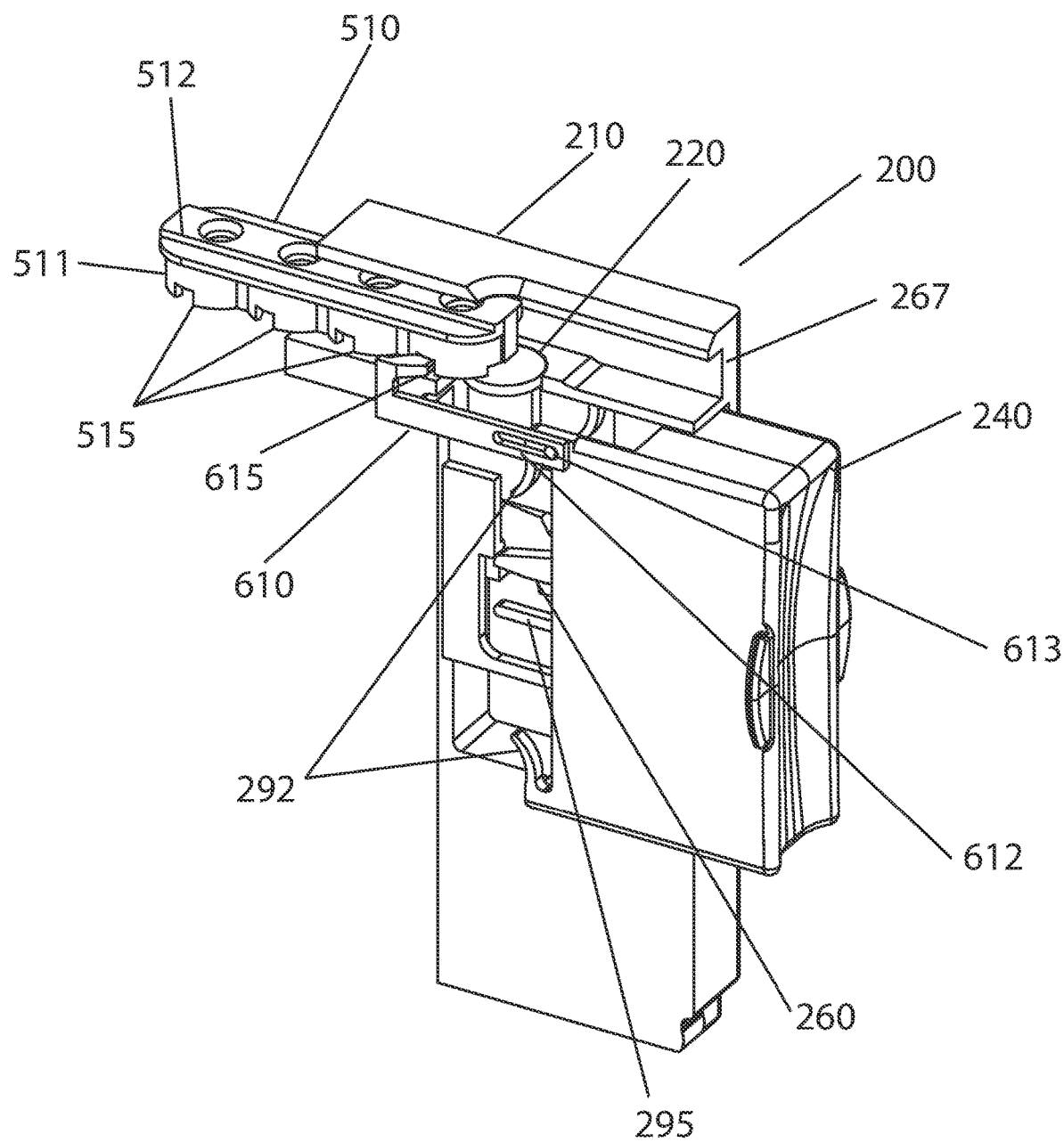
FIG. 16 shows another cutaway view of a cartridge in a handheld device.
Figure 17:
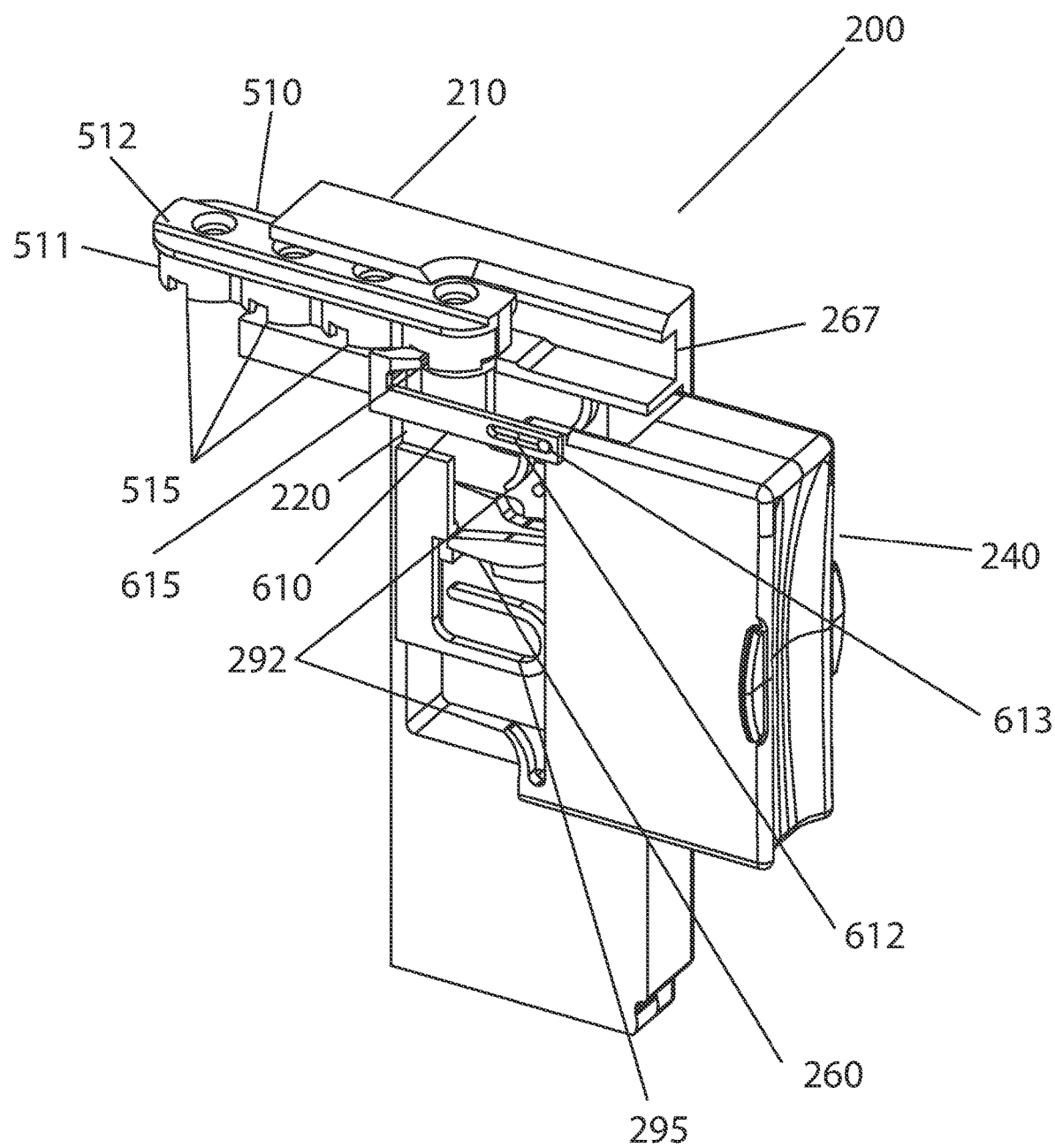
FIG. 17 shows another cutaway view of a cartridge in a handheld device.

Thereafter, dispense button 240 is thus extended or withdrawn from shell 210, as shown in FIG. 16, during the "make ready" step. As dispense button 240 is extended, the longitudinal slide arm 610 translates with the dispense button 240 which in turn advances the cartridge 510 by movement of the slide arm finger member 615 interfacing with the notch 515. Also shown in cutaway view in FIG. 16, and described in greater detail above, plunger escapement member 260 and plunger return spring 295 are partially shown within shell 210. As described above, escapement 260 is movable (rotatable and/or translatable) about an axis 265 within shell 210 and may comprise a plurality of ramp surfaces 270. Each ramp 270 is configured to provide a defined action when drive member 250 (not shown in FIG. 16 but see earlier figures) translates along its surface. For example, the number of plunger escapement member 260 ramps 270 may be two and the first and second ramps may each be disposed on different sides of plunger escapement member 260. In other embodiments, as also described prior, the plunger escapement member 260 may be comprised at least three ramps (e.g., 270-272) of which one is configured as a reset ramp to return the assembly to an original static position. At the end of the "make ready" step, as shown in FIG. 17, the first unit dose form 230 on the cartridge 510 is centered over the plunger 220 and is ready to be dispensed as described above and shown in FIG. 4 onward.

Figure 18:
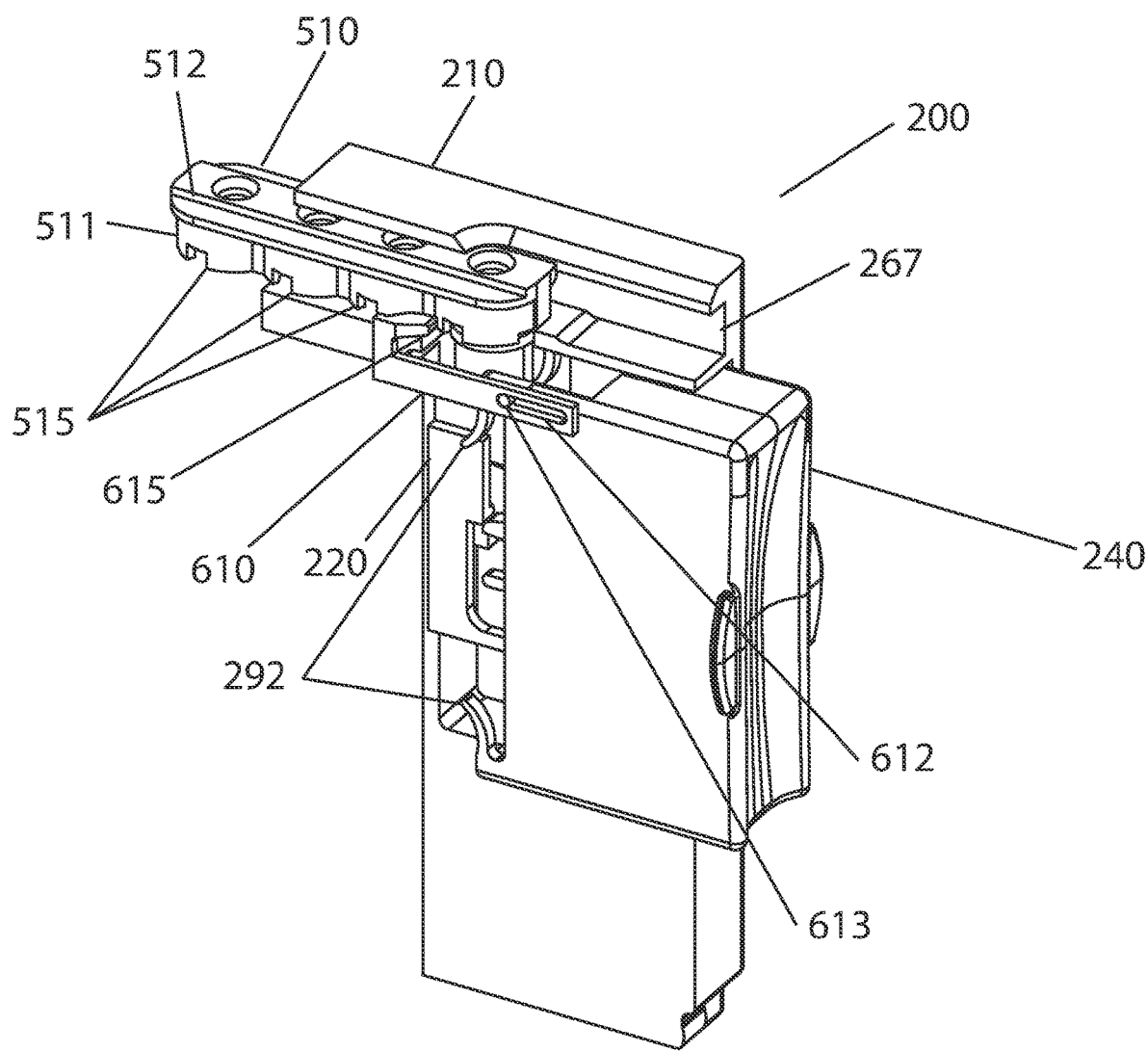
FIG. 18 shows another cutaway view of a cartridge in a handheld device.

During the "dispense actuation stage", the dispense button 240 is retracted (e.g., pushed inwardly by a user) back into the shell 210 as shown in FIG. 18. While it is not shown in FIG. 18, plunger 220 is crushing the unit dose form 230 as shown in FIGS. 4A-D. As the dispense button 240 retracts into the shell 210, the longitudinal slide arm 610 translates with the dispense button 240 to translate the slide arm finger member 615 towards the next notch 515 that is adjacent to the subsequent blister chamber 511 containing the next unit dose form 230 of cartridge 510. At the end of the "dispense actuation stage" with the dispense button 240 fully retracted into the shell 210, the slide arm finger member 615 is in position with the subsequent notch 515 so that the next "make ready" step will advance the subsequent unit dose form 230 into position adjacent to plunger 220. Also, as shown in FIGS. 16-18, and described earlier, at the end of the dispense stage, when dispense button 240 is released by the user, one or more dispense button return springs 292 may be used to push dispense button 240 outward from shell 210.

Figure 19:
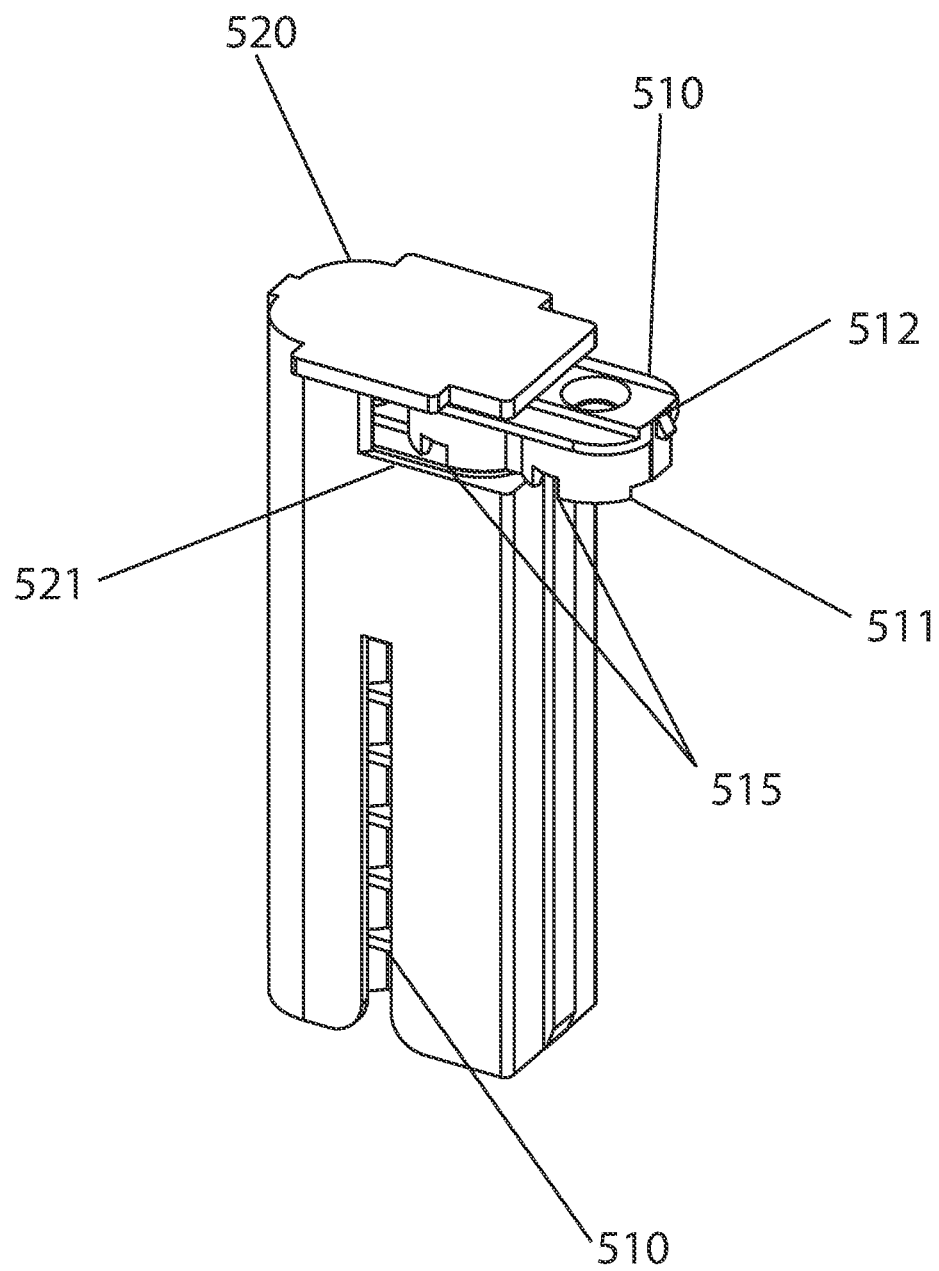
FIG. 19 shows an exemplary dip of unit dose cartridges.

In yet other multidose embodiments, a separate housing comprising a clip 520 may be configured to hold more than one cartridge 510 as shown for example in FIG. 19. Clip 520 may hold the cartridges 510 in a preferred embodiment as a vertical array, but a horizontal or circular array or any other suitable shape is contemplated herein. Each clip 520 may also include a slotted outlet 521 which allows for the extraction of the cartridge 510 from the interior of clip 520.

Figure 20:
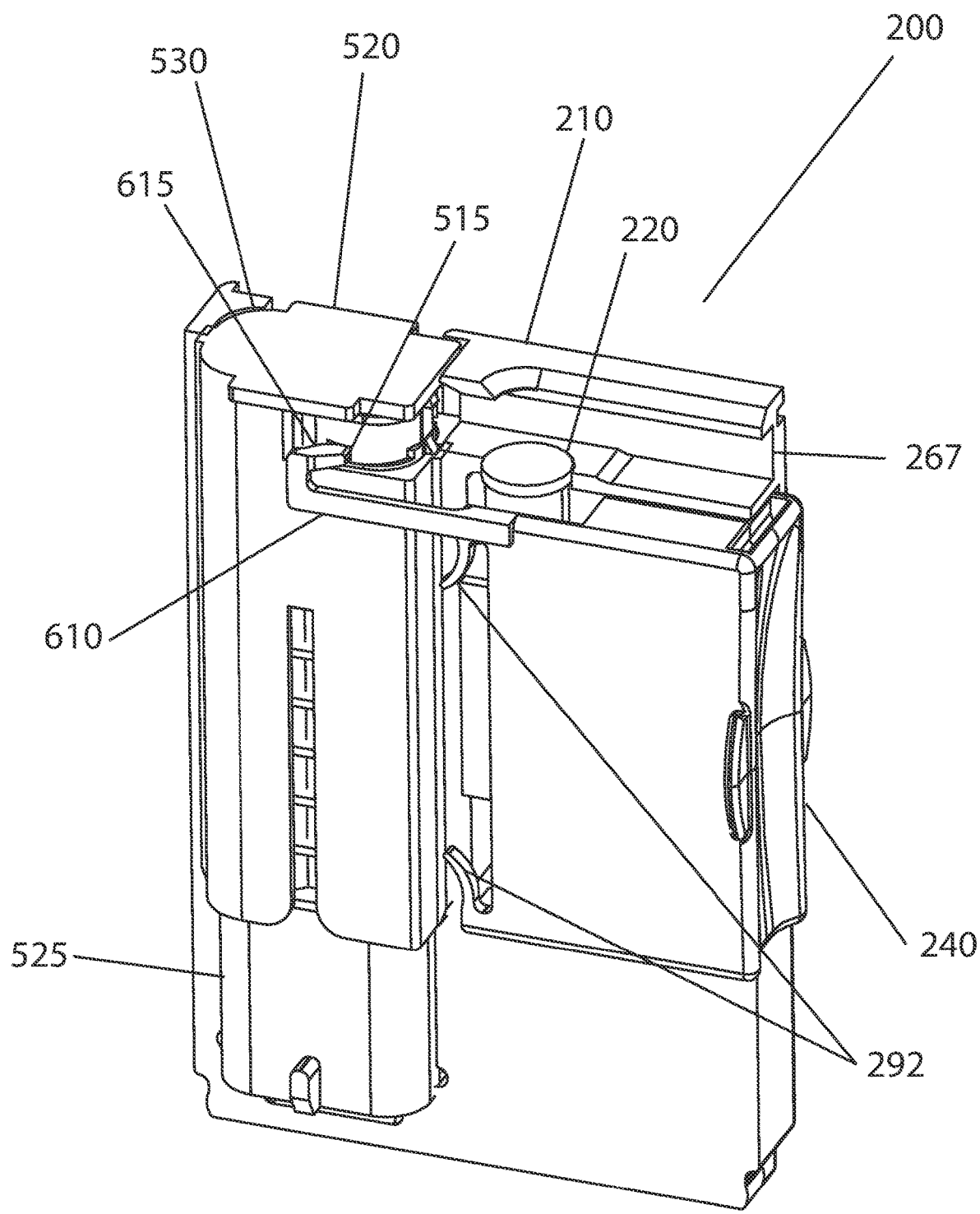
FIG. 20 shows a cutaway view of a clip of cartridges in a handheld device.

In other exemplary multidose assemblies as shown in FIGS. 19-21 include a clip 520 comprising a housing containing more than one, and preferably several, cartridges 510 that supply doses to assembly 200. As shown, clip 620 is configured as a vertical housing which contains stackable cartridges 510 as dual dose arrays with two blister chambers 511. Other configurations are possible including cartridges configured as stackable linear arrays of three or four or more blister chambers 511, or as circular arrays provided as stackable disks loadable into clip 520.

In these embodiments, shell 210 of assembly 200 includes an expanded housing which includes a clip chamber 530 configured to receive clip 520. Each cartridge 510 is retrievable from the clip 520 via a slotted outlet 521. With reference to FIG. 20, as shown in cutaway view, longitudinal slide arm 610 and slide arm finger member 615 engage notch 515 of blister chamber 511 thus drawing cartridge 520 into alignment with plunger 220 as described prior.

Figure 21A:
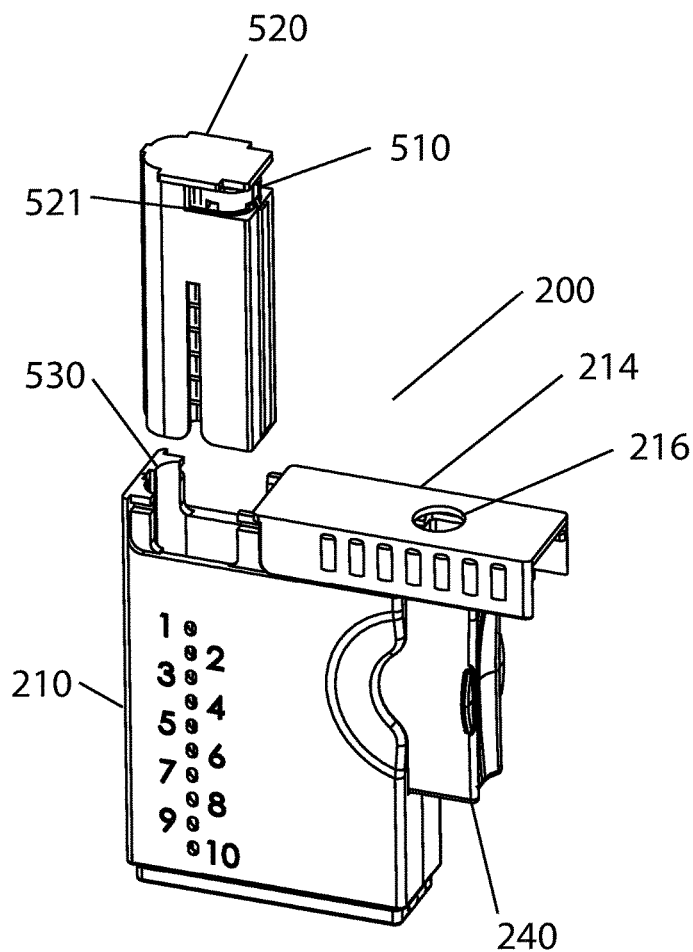
FIGS. 21A and B shows views of a clip of cartridges in a handheld device.
Figure 21B:
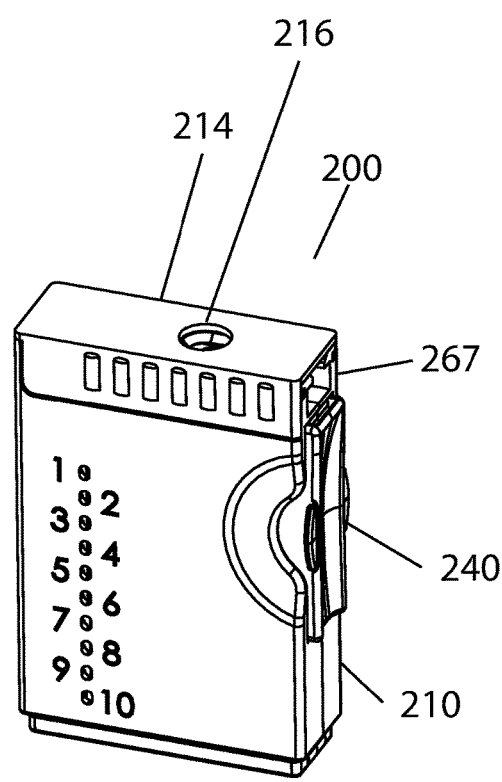

As shown in FIGS. 21A-B, shell 210 may further incorporate a slidable clip retainer 214 which in its closed position (FIG. 218) serves to enclose and secure clip 520 within shell 210. Note that in the embodiment shown, retainer 214 is of a length that also covers cartridge alignment channel 267 of shell 210 in which case retainer 214 includes an outlet 216 through which medicament 235 exits the assembly upon dispensation of a unit dose 230 during the "dispense actuation stage."

Clip retainer 214 may further include a cartridge ejector 216 comprised of a tab located on an internal surface of retainer 214 configured to engage cartridge 510. Following dispense, retainer 214 is slidably withdrawn (to the right in FIGS. 21A-B) which pulls used cartridge 510 away from plunger 220, thus allowing for its removal and disposal. A subsequent cartridge 510 within clip 520 may then be advanced through the clip 520. Alternatively, a subsequent cartridge 510 could push the previous spent cartridge out when advanced to the firing position. In another embodiment, the spent cartridge 510 may be ejected using a slide or lever separate from clip retainer 214 that is independently actuated by the user.

What is claimed is:

1. A handheld assembly (200) for dispensing a medicament (235) to a subject, the assembly comprising:
   a shell (210) housing at least partially a dispense button (240), a drive member in communication with the dispense button, a plunger (220), and rotatable escapement member (260) having at least one ramp surface (270);
   a unit dose cartridge (510) comprising more than one cylindrical blister chambers (511) each configured to house a unit dose form (230) wherein each unit dose form contains a medicament;

wherein the shell further comprises a cartridge alignment channel (267) open on opposite ends and configured to slidably accept the unit dose cartridge; and wherein depressing the dispense button causes the drive member to translate along a ramp of the plunger escapement member extending the plunger to express the unit dose form.

2. The assembly of claim 1, wherein the dispense button further comprises a longitudinal slide arm (610) having a slotted recess (612) on an adjacent end and a slide arm finger member (615) on the distal end, wherein the slotted recess is in communication with the dispense button and the slide arm finger member is configured to slidably advance the unit dose cartridge when the dispense button is withdrawn.

3. The assembly of claim 2, wherein the slide arm finger member is configured to translate to a subsequent cylindrical blister chamber when the dispense button is depressed.

4. The assembly of claim 2, wherein a cylindrical blister chamber (511) further comprises a notch (515) located on a sidewall of said cylindrical blister chamber (511) and which is configured to engage a portion of the slide arm finger member.

5. The assembly of claim 1, wherein the cartridge comprising a plurality of cylindrical blister chambers is molded as a single unit.

6. The assembly of claim 1, wherein the unit dose form further comprises an internal piercing member with an internal channel.

7. A handheld assembly (200) for dispensing a medicament (235) to a subject, the assembly comprising:
 a shell (210) configured for housing components of the handheld assembly;
 a unit dose cartridge comprising more than one cylindrical blister chambers (512) configured to each house a unit dose form (230) wherein each unit dose form contains a medicament;
 a plunger (220) at least partially enclosed within the shell and extending from the shell and configured to express a unit dose form;
 a dispense button (240) at least partially enclosed within the shell and extending from the shell and in slidable communication with the shell;
 a drive member (250) located within the shell and in communication with the dispense button;
 a plunger escapement member (260) movable about an axis (265) within the shell and having more than one ramp (270) wherein each ramp has a predetermined profile (275);
 wherein a first motion of the dispense button causes the drive member to translate along a first ramp of the plunger escapement member readying the assembly for dispense, and
 wherein a second motion of the dispense button causes the drive member to translate along a second ramp of the plunger escapement member extending the plunger to express the unit dose form.

8. The assembly of claim 7, wherein the drive member is comprised of a protruding body integral with or attached to the dispense button.

9. The assembly of claim 7 further comprising a plunger escapement member return spring disposed within the shell.

10. The assembly of claim 7, further comprising a dispense button return spring disposed within the shell.

11. The assembly of claim 7, wherein the number of plunger escapement member ramps is two and the first and second ramps are each disposed on different sides of the plunger escapement member.

12. The assembly of claim 7, wherein the plunger further comprises a planar hold surface disposed within the shell that maintains the plunger in a dispense state for a predetermined time at the end of dispense.

13. The assembly of claim 7, wherein the plunger escapement member further comprises at least three ramps of which one is configured as a reset ramp to return the assembly to an original static position.

14. The assembly of claim 7, wherein at least one of the ramps of the plunger escapement member has a predetermined profile with more than one discrete section.

15. The assembly of claim 7, wherein the unit dose form further comprises an internal piercing member.

16. The assembly of claim 15, wherein the internal piercing member further comprises an internal channel.

17. A handheld assembly (200) for dispensing a medicament (235) to a subject, the assembly comprising:
 a shell (210) configured for housing components of the handheld assembly;
 a clip receivable within the shell, the clip comprising a housing containing more than one stackable unit dose cartridge (510) wherein each cartridge is comprised of more than one cylindrical blister chambers (511) configured to each house a unit dose form (230) wherein each unit dose form contains a medicament;
 a plunger (220) at least partially enclosed within the shell and extending from the shell and configured to express a unit dose form within the cartridge;
 a dispense button (240) at least partially enclosed within the shell and extending from the shell and in slidable communication with the shell;
 a drive member (250) located within the shell and in communication with the dispense button;
 a plunger escapement member (260) movable about an axis (265) within the shell and;
 wherein the plunger escapement member comprises a plurality of ramp surfaces (270).

18. The assembly of claim 17, wherein the unit dose form further comprises an internal piercing member with an internal channel.

19. The assembly of claim 17, wherein the number of plunger escapement member ramps is two and the first and second ramps are each disposed on different sides of the plunger escapement member.

20. The assembly of claim 17, wherein the plunger escapement member further comprises at least three ramps of which one is configured as a reset ramp to return the assembly to an original static position.

* * * * *